(12) United States Patent
Gambhir et al.

(10) Patent No.: US 8,795,628 B2
(45) Date of Patent: Aug. 5, 2014

(54) MOLECULAR IMAGING OF LIVING SUBJECTS USING RAMAN SPECTROSCOPY AND LABELED RAMAN NANOPARTICLES

(75) Inventors: Sanjiv S. Gambhir, Portola Valley, CA (US); Shay Keren, Haifa (IL); Ian Walton, Redwood City, CA (US); David Guagliardo, Chicago, IL (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 310 days.

(21) Appl. No.: 12/598,780

(22) PCT Filed: May 5, 2008

(86) PCT No.: PCT/US2008/062649
§ 371 (c)(1),
(2), (4) Date: Nov. 4, 2009

(87) PCT Pub. No.: WO2009/020680
PCT Pub. Date: Feb. 12, 2009

(65) Prior Publication Data
US 2010/0166650 A1    Jul. 1, 2010

Related U.S. Application Data

(60) Provisional application No. 60/927,574, filed on May 4, 2007.

(51) Int. Cl.
*A61K 51/00* (2006.01)
*A61K 49/00* (2006.01)

(52) U.S. Cl.
USPC ......... 424/1.69; 424/1.11; 424/1.53; 424/9.1; 424/9.3

(58) Field of Classification Search
USPC ......... 600/473, 476; 424/1.53, 1.69; 436/514, 436/518, 523–526
See application file for complete search history.

(56) References Cited

U.S. PATENT DOCUMENTS

| | | | |
|---|---|---|---|
| 2004/0073120 A1 | 4/2004 | Motz et al. | |
| 2005/0143662 A1* | 6/2005 | Marchitto et al. | 600/473 |
| 2006/0054506 A1* | 3/2006 | Natan et al. | 205/112 |
| 2007/0238953 A1* | 10/2007 | Lucassen et al. | 600/407 |
| 2009/0304581 A1* | 12/2009 | Scheinberg et al. | 424/1.53 |

* cited by examiner

*Primary Examiner* — Michael G Hartley
*Assistant Examiner* — Jagadishwar Samala
(74) *Attorney, Agent, or Firm* — Thomas|Horstemeyer, LLP

(57) ABSTRACT

Methods of imaging a living host using Raman nanoparticles; methods of generating a true image of a living host having been administered Raman nanoparticles; methods of multiplex imaging of a living host using a plurality of Raman nanoparticles; methods of generating multimodality images by combining Raman images with other functional/anatomical images; labeled Raman nanoparticles; and the like, are provided.

20 Claims, 18 Drawing Sheets

Raman Shift cm-1

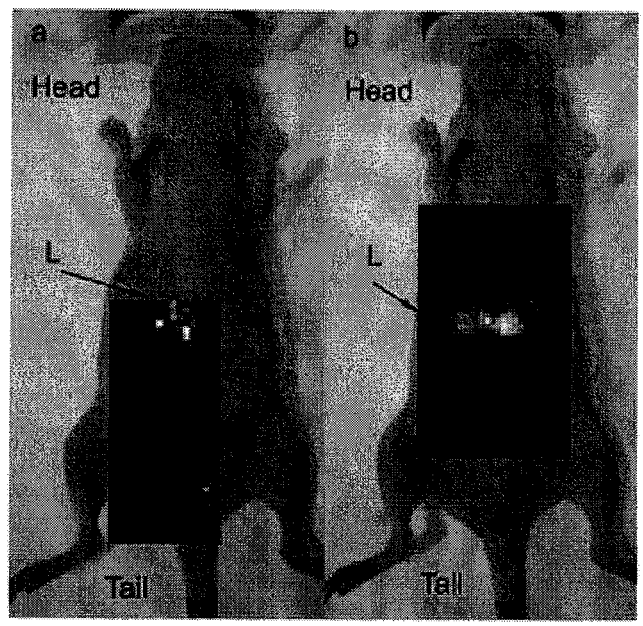
Fig. 1-14
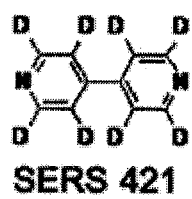
SERS 421
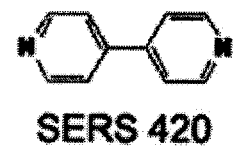
SERS 420
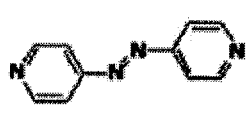
SERS 481
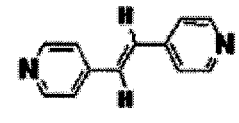
SERS 440
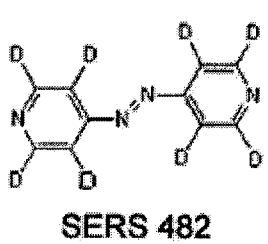
SERS 482
Fig. 1-15

(From top to bottom: Ex-vivo RGD nanotubes in tumor, In-vivo RGD nanotubes in tumor, In-vivo plain nanotubes in tumor, background, and Ex-vivo plain nonotubes in tumor))

MOLECULAR IMAGING OF LIVING SUBJECTS USING RAMAN SPECTROSCOPY AND LABELED RAMAN NANOPARTICLES

CROSS-REFERENCE TO RELATED APPLICATION

This application claims priority to "MOLECULAR IMAGING OF LIVING SUBJECTS USING RAMAN SPECTROSCOPY AND LABELED RAMAN NANOPARTICLES," having serial number PCT/US2008/62649, filed on May 5, 2008. This application claims priority to the following U.S. provisional application: "MOLECULAR IMAGING OF LIVING SUBJECTS USING RAMAN SPECTROSCOPY," having Ser. No. 60/927,574, filed on May 4, 2007; which is entirely incorporated herein by reference.

STATEMENT REGARDING FEDERALLY SPONSORED RESEARCH OR DEVELOPMENT

This invention(s) was made with government support under Grant No.: U54 CA119367 awarded by the NCI CCNE. The government has certain rights in the invention(s).

BACKGROUND

Molecular imaging of living subjects provides the ability to study cellular and molecular processes that have the potential to impact many facets of biomedical research and clinical patient management. Imaging of small animal models is currently possible using positron emission tomography (PET), single photon emission computed tomography (SPECT), magnetic resonance imaging (MRI), computed tomography (CT), optical bioluminescence and fluorescence, high frequency ultrasound, as well as several other emerging modalities. However, no single modality currently meets the needs of high sensitivity, high spatial and temporal resolution, high multiplexing capacity, low cost, and high-throughput.

Fluorescence imaging, in particular, has significant potential for in vivo studies but is limited by several factors. These include a limited number of fluorescent molecular imaging agents available in the near infra-red (NIR) window with large spectral overlap between them which restricts the ability to interrogate multiple targets simultaneously (multiplexing). In addition, background autofluorescence emanating from superficial tissue layers restricts the sensitivity and the depth to which fluorescence imaging can be employed. Moreover, rapid photobleaching of fluorescent molecules limits their useful lifetime and prevents studies of prolonged duration. We have therefore been attempting to develop new strategies that may solve some of the limitations of fluorescence imaging in living subjects.

Raman spectroscopy can differentiate the spectral fingerprint of many molecules, resulting in very high multiplexing capabilities. Narrow spectral features are easily separated from the broadband autofluorescence since Raman is a scattering phenomenon, as opposed to absorption/emission in fluorescence, and Raman active molecules are more photostable compared with fluorophores that are rapidly photobleached. Unfortunately, the precise mechanism for photobleaching is not well understood. However, it has been linked to a transition from the excited singlet state to the excited triplet state. Photobleaching is significantly reduced for single molecules adsorbed onto metal particles due to the rapid quenching of excited electrons by the metal surface, thus preventing excited-state reactions and hence photobleaching. However, the inherently weak magnitude of the Raman effect (approximately one photon is inelastically scattered for every $10^7$ elastically scattered photons) limits the sensitivity, and as a result the biomedical applications of Raman spectroscopy. The discovery of the surface enhanced Raman scattering (SERS) phenomenon offers an exciting opportunity to overcome this lack of sensitivity and introduce Raman spectroscopy into new fields. SERS is a plasmonic effect where molecules adsorbed onto nano-roughened noble metal surfaces experience a dramatic increase in the incident electromagnetic field resulting in high Raman intensities comparable to fluorescence.

Single walled carbon nanotubes (SWNT) also show an intense Raman peak produced by the strong electron-phonon coupling which causes efficient excitation of tangential vibration in the nanotubes quasi one-dimensional structure upon light exposure. Recent demonstration of tumor targeting using radiolabeled SWNT combined with low toxicity effects and rapid renal excretion suggest carbon nanotubes may also become promising molecular imaging agents for living subjects.

SUMMARY

Briefly described, embodiments of this disclosure include methods of imaging a living host using Raman nanoparticles; methods of generating a true image of a living host having been administered Raman nanoparticles; methods of multiplex imaging of a living host using a plurality of Raman nanoparticles; methods of generating multimodality images by combining Raman images with other functional/anatomical images; labeled Raman nanoparticles; and the like.

One exemplary method for imaging a living host, among others, includes: providing a living host with a first type of Raman nanoparticle; and imaging the living host with a Raman imaging system.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 1-1a illustrates a Raman spectrum acquired from first subcutaneous injection of S421 SERS nanoparticles. The software has assigned the color red for this particular Raman spectrum. FIG. 1-1b illustrates a Raman spectrum acquired from second subcutaneous injection of S440 SERS nanoparticles. The software has assigned the color green for this particular Raman spectrum. FIG. 1-1c is a digital image that illustrates Raman spectrum acquired from the third subcutaneous injection of an equal mix of S421 and S440. Notice how this spectrum represents an equal mix of both individual spectrums as if they had been overlaid. As a result, the color yellow is calculated by the analysis software to represent an equal mix of the red (S421) and green (S440) SERS nanoparticles in the map to the right.

FIG. 1-2 is a digital image illustrating the evaluation of multiplexing 4 different concentrations of SERS nanoparticles in-vivo. FIG. 1-2a illustrates a Raman map of 4 different SERS particles injected subcutaneously. The fifth subcutaneous injection represented by a purple color at the far right is a mixture of the different four SERS particles with different concentrations. FIG. 1-2b illustrates a Raman map depicting the SERS 482 nanoparticles, this injection site is assigned the color green in panel a. Notice how there is faint pixel brightness in the fifth injection site, corresponding to the least concentration of this SERS particle in the mixture. FIG. 1-2c illustrates a Raman map depicting the SERS 420 nanoparticles, this injection site is assigned the color red in panel a. Notice how there is intense pixel brightness in the fifth injection site corresponding to the most concentration of this SERS particle in the mixture. FIG. 1-2d illustrates a Raman map depicting SERS 481 nanoparticles, this injection site is assigned the color yellow in panel a. Notice how the fifth injection site shows the third brightest pixel intensity corresponding to the second least concentrated of the SERS particle mixture. FIG. 1-2e illustrates a Raman map depicting the SERS 421 nanoparticles, this injection site is assigned the color blue in panel a. Notice how the fifth injection site shows the second brightest pixel intensity corresponding to the second most concentrated of the SERS particle mixture.

FIG. 1-3 illustrates the pharmacokinetics of embodiments of SERS nanoparticles and single-wall nanotubes (SWNTs) in the liver (data acquisition starts at 10 seconds, zero accumulation at time point zero data not shown). FIG. 1-3a illustrates the accumulation of non-pegylated SERS versus 5 kD PEG SERS nanoparticle in liver of nude mouse. The graph depicts the mean normalized concentration of SERS nanoparticles in three mice±s.e.m. FIG. 1-3b illustrates the accumulation of non-pegylated SERS versus 20 kD PEG SERS nanoparticle in liver of nude mouse. The graph depicts the mean normalized concentration of SERS nanoparticles in three mice±s.e.m. FIG. 1-3c illustrates the pharmacokinetics of nanotubes in liver evaluated over 90 minutes post tail-vein injection. The graph depicts the mean normalized concentration of nanotubes in four mice±s.e.m. Notice gradual increase of SWNT accumulation in liver after 30 minutes post injection.

FIGS. 1-4 are digital images that illustrate a raster-scan image of mouse liver using Raman spectroscopy in conjunction with SERS nanoparticles. FIG. 1-4a illustrates a whole-body map (1 mm steps) of nude mouse 2 hours after tail-vein injection of SERS nanoparticles. Notice how most of the SERS particles accumulated in the liver (L arrow) resulting in a well defined image. FIG. 1-4b illustrates a map of liver (750 micron steps) showing higher definition of liver (L arrow) and slight distinction between the two liver lobes.

FIG. 1-5 illustrates the setup of the Raman microspectroscopy system and schematic of Raman nanoparticles used for in-vivo imaging. FIG. 1-5(a) is a digital image of a Raman microscope adopted for small animal imaging with mouse positioned supine on an x-y translation stage. The liver is illuminated with a 785 nm excitation laser. FIG. 1-5(b) illustrates a schematic of SERS active nanoparticles (Nanoplex™ Biotag) showing a gold core and a layer of Raman tag encapsulated in a glass shell. FIG. 1-5(c) illustrates a schematic of single wall nanotube showing a mean diameter of 3 nm and a length of approximately 200 nm (not drawn to scale).

FIG. 1-6 illustrates transmission electron microscopy of SERS nanoparticles and atomic force microscopy image of SWNTs. FIG. 1-6(a) illustrates a transmission electron microscopy image of SERS nanoparticles. The diameter distribution of gold core and glass shell showed a mean value of 50 nm and 120 nm respectively. FIG. 1-6(b) illustrates an atomic force microscopy image of SWNTs. Notice that the nanotubes are approximately 200 nm in length with a diameter of 3 nm in diameter.

FIG. 1-7 illustrates a comparison of Raman spectra produced from a pure sample of SWNTs, and a sample of one flavor of SERS nanoparticles labeled S420. Notice the distinctly inherent Raman peak at 1593 cm-1 produced from a pure sample of SWNTs. The SERS nanoparticles however display multiple narrow peaks based on the particular Raman active layer coupled to the gold core. These variously distributed narrow peaks allow for multiplexing of the different Raman flavors found on the Nanoplex™ Biotags.

FIG. 1-8 illustrates a comparison of Raman spectra produced from a sample of SERS nanoparticles, SERS particles in the liver of a mouse, a sample of mouse serum, the background image taken on the mouse before SERS nanoparticle injection, and the matrigel used in the subcutaneous injections. Notice how the Raman spectrum of the pure sample of SERS particles correlates well with the Raman spectrum of the liver in the mouse after IV injection of SERS particles.

FIG. 1-9 is a graph that illustrates the linearity and sensitivity of SERS nanoparticles detected ex-vivo. Ex-vivo measurements of serially diluted SERS nanoparticles show high linearity of the calculated concentration with $R^2=0.997$ and a detection limit of 600 particles.

FIG. 1-10 is a graph illustrating ex-vivo multiplexing. The graph illustrates a mixture of two different SERS nanoparticles with concentrations ranging from 1% to 99% showing calculated concentration with mean error of 14.25%.

FIG. 1-11a are digital images that illustrates a digital photograph of mouse depicting tumor area (black square) and corresponding Raman images acquired 24 hours post SWNT injection by raster scan with 750 μm steps. Notice the accumulation of RGD SWNTs in the tumor area as opposed to the plain non-targeted SWNTs that show little to no accumulation in the tumor area. FIG. 1-11b illustrates the Raman spectral analysis of RGD nanotubes and plain non-targeted nanotubes within the tumor at 24 hours post SWNT injection. The graphed data show a significant increase (*indicates $p<0.05$) in Raman signal in mice (n=3 per group) injected with RGD nanotubes as opposed to mice injected with plain nanotubes, thus indicating accumulation of RGD SWNT to tumor site. This quantitative data supports the Raman images displayed in panel FIG. 1-11a.

FIG. 1-12 is a graph that illustrates Raman spectra of four different SERS nanoparticles used in multiplexing experiment.

FIG. 1-13 is a graph that illustrates Raman spectra of SERS nanoparticles accumulating in the liver over time. Note that the Raman signal (counts) gradually increases over time as the SERS particles arrive in the liver over 5 minutes. Note that the spectra acquired before injection shows no correlation to the SERS spectra seen above (data not shown).

FIG. 1-14 is a digital image of mouse liver using Raman imaging in conjunction with SWNT. FIG. 1-14(a) is a Raman image taken 2 hours after tail-vein injection of nanotubes overlaid on a photograph of the mouse. Notice the increased accumulation of nanotubes in liver (L arrow) as well as lower accumulation in the peritoneal cavity. FIG. 1-14(b) is a Raman image taken 72 hours after tail-vein injection of nanotubes. Notice the increased intensity of Raman signal in the better defined liver (L arrow) with little to no accumulation in the peritoneal cavity as compared to the 2 hour image.

FIG. 1-15 illustrates chemical structures of Raman active tags on different SERS particles used in this study. Each molecule has a different configuration of bonds that vibrate differently resulting in various Raman spectra ideal for multiplexing. Notice how SERS 421 is the deuterated form of SERS 420 and SERS 482 is the deuterated form of SERS 481, where D=deuterium.

FIG. 2-1 illustrates the pharmacokinetics of RGD SWNTs (n=3) and plain non-targeted SWNTs (n=3) in the tumor of nude mice over time. Notice the accumulation of RGD nanotubes (gray diamonds) in the tumor slightly increases over time remaining within the tumor area. Plain nanotubes (open-faced squares) appear to initially arrive in the tumor with a rapid decrease after 20 minutes post-injection. Data are presented as mean±standard error, and * indicates p<0.05.

FIG. 2-2 illustrates raster-scan digital images of tumor area (750 μm steps) using Raman spectroscopy in conjunction with SWNTs. The grayscale bar to the right depicts the Raman intensity where white represents the maximum intensity and black represents no intensity. FIG. 2-2(A) is a digital photograph of tumor bearing mouse depicting tumor area scanned with Raman spectroscopy (black box). FIG. 2-2(B) illustrates a panel of tumor maps from mouse receiving RGD nanotubes at various time points post injection starting from left to right with 2 h, 8 h, 24 h, 48 h, and 72 h. FIG. 2-2(C) illustrates a panel of tumor maps from mouse receiving plain nanotubes at various time points post injection starting from left to right with 2 h, 8 h, 24 h, 48 h, and 72 h. Notice how the panel of tumor maps in panel B of FIG. 2-3 from the mouse that received RGD nanotubes shows a continued accumulation of nanotubes in the tumor area over 72 hours, as opposed to panel c which shows no defined accumulation of nanotubes in the tumor area of a mouse that received plain nanotubes.

FIG. 2-3 illustrates Raman spectral analysis of RGD nanotubes and plain non-targeted nanotubes within the tumor over three days post injection (error bars represent s.e.m.). The graphed data show a significant difference (* indicates p<0.05) between mice injected with RGD nanotubes and mice injected with plain nanotubes at all time points post injection. Very little Raman signal was seen throughout the control group therefore a y-axis break was placed between 0.0002 and 0.01 to visualize lower nanotube concentration in tumors of mice receiving plain nanotubes.

FIG. 2-4 illustrates Raman spectral analysis comparing accumulation of RGD nanotubes within the tumor area on the right shoulder and the contralateral left shoulder (no tumor) of nude mice (error bars represent s.e.m.). Notice the significant increase (* indicates p<0.05) of RGD nanotube accumulation within the tumor area as opposed to the contralateral shoulder at all time points over three days.

FIG. 2-5 illustrates Raman spectrum acquired from in-vivo (red) and ex-vivo (green) tumors at 72 hours in both experimental and control groups of mice. Notice how the g-band Raman peak (~1593 cm$^{-1}$) is prominently pronounced in the experimental group where mice received RGD conjugated nanotubes. Conversely, there is no g-band Raman peak associated with the nanotubes seen in either the in-vivo (blue) or ex-vivo (light blue) tumors taken from the mice that received non-targeted plain nanotubes. The spectrums given from the control mice resemble the background spectrum (gray) taken of the tumors before nanotube injection.

FIG. 2-6 illustrates Raman spectral analysis of RGD and plain nanotube accumulation within various tissues from experimental and control mice (error bars represent s.e.m.). FIG. 2-6(A) illustrates Raman data of various excised tissues at 72 hours post nanotube injection. Excised tumor data shows more accumulation of RGD nanotubes within tumor tissue than plain nanotubes at 72 hours, supporting in-vivo data shown previously. The graph also depicts more accumulation of plain nanotubes within the excised liver and spleen in comparison to the mice that received RGD conjugated nanotubes. FIG. 2-6(B) illustrates in-vivo Raman data of RGD nanotubes and plain non-targeted nanotubes within the liver over three days post injection. Notice how the 72 hour time point shows roughly twice as much nanotube accumulation in the liver of mice receiving plain nanotubes, correlating with the 72 hr ex-vivo data in panel A. Significant differences in nanotube accumulation within the liver were observed at 24 and 72 hours post injection with a p<0.05 depicted with *.

FIG. 2-7 illustrates Raman digital image mapped from excised tumor tissue at 72 hours post nanotube injection. The grayscale bar to the right depicts the Raman intensity where white represents the maximum intensity and black represents no intensity. FIG. 2-7(A) illustrates tumor excised from experimental mouse that received RGD conjugated nanotubes. FIG. 2-7(B) illustrates tumor excised from control mouse that received plain non-targeted nanotubes. Notice the well defined nanotube accumulation in the tumor that received RGD nanotubes.

FIG. 2-8 illustrates Raman digital images mapped from liver and spleen at 72 hours post nanotube injection. The grayscale bar to the right depicts the Raman intensity where white represents the maximum intensity and black represents no intensity. FIG. 2-8(A) illustrates in-vivo Raman image of liver at 72 hours post nanotube injection. FIG. 2-8(B) illustrates ex-vivo Raman image of liver at 72 hours post nanotube injection corresponding to image in panel A. FIG. 2-8 C) illustrates ex-vivo Raman image of spleen at 72 hours post nanotube injection. In-vivo liver image is less detailed than ex-vivo liver image. This is due to scattering of light and low light penetration through the skin as well as breathing motion in a living mouse.

DETAILED DESCRIPTION

Figure 1:
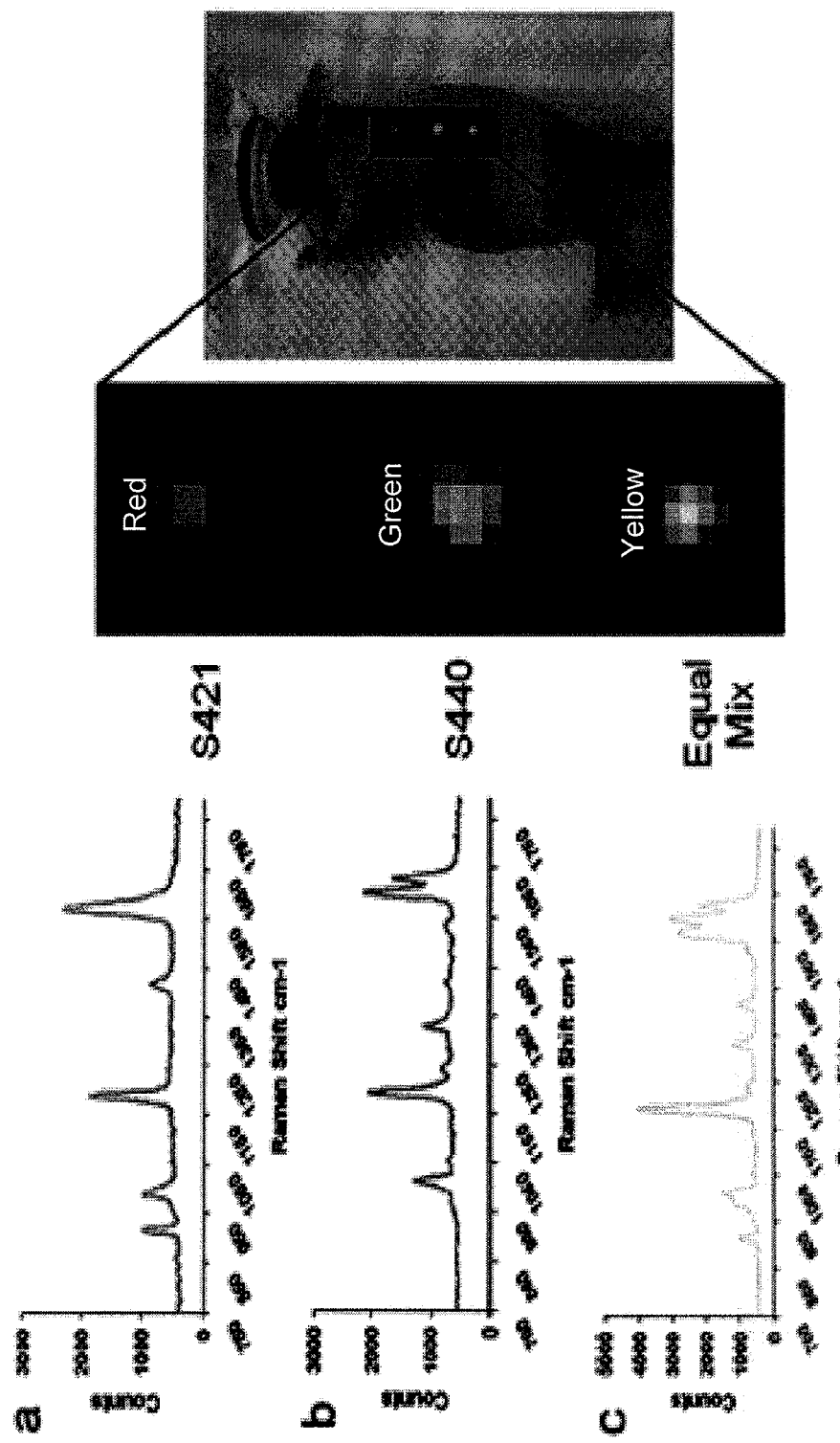
FIG. 1-1 illustrates an evaluation of a multiplexing experiment using embodiments of the present disclosure.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of synthetic organic chemistry, biochemistry, biology, molecular biology, recombinant DNA techniques, pharmacology, imaging, and the like, which are within the skill of the art. Such techniques are explained fully in the literature. In particular, See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. (1985)); "Transcription and Translation" (B. D. Hames & S. J. Higgins eds. (1984)); "Animal Cell Culture" (R. I. Freshney, ed. (1986)); "Immobilized Cells and Enzymes" (IRL Press, (1986)); B. Perbal, "A Practical Guide To Molecular Cloning" (1984), each of which is incorporated herein by reference.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

Definitions

In describing and claiming the disclosed subject matter, the following terminology will be used in accordance with the definitions set forth below.

The term "Surface-Enhanced Raman Scattering (SERS)" refers to the increase in Raman scattering exhibited by certain molecules in proximity to certain metal surfaces. (see, U.S. Pat. No. 5,567,628) The SERS effect can be enhanced through combination with the resonance Raman effect. The surface-enhanced Raman scattering effect is even more intense if the frequency of the excitation light is in resonance with a major absorption band of the molecule being illuminated. In short, a significant increase in the intensity of Raman light scattering can be observed when molecules are brought into close proximity to (but not necessarily in contact with) certain metal surfaces. The metal surfaces need to be "roughened" or coated with minute metal particles. Metal colloids also show this signal enhancement effect. The increase in intensity can be on the order of several million-fold or more.

The term "reporter compound" can refer to a Raman-active label. The term "Raman-active label" can refer to a substance that produces a detectable Raman spectrum, which is distinguishable from the Raman spectra of other components present, when illuminated with a radiation of the proper wavelength.

As used herein, the terms "Raman nanoparticle", "imaging probe", "imaging agent", or "imaging compound" refer to the compounds or structures of the present disclosure that are capable of serving as imaging agents either alone or in combination with attached molecules (e.g., proteins, peptides, small organic molecules, and the like). In particular non-limiting embodiments the imaging probes or imaging agents of the present disclosure can be imaged using a Raman imaging system.

The term "administration" refers to introducing a compound of the present disclosure into a host. The preferred route of administration of the compounds is intravenous. However, any route of administration, such as oral, topical, subcutaneous, peritoneal, intraarterial, inhalation, vaginal, rectal, nasal, introduction into the cerebrospinal fluid, or instillation into body compartments can be used.

In accordance with the present disclosure, "a detectably effective amount" of the imaging agent (e.g., Raman nanoparticle) of the present disclosure is defined as an amount sufficient to yield an acceptable image using equipment that is available for pre-clinical use. A detectably effective amount of the imaging agent of the present disclosure may be administered in more than one injection. The detectably effective amount of the imaging agent of the present disclosure can vary according to factors such as the degree of susceptibility of the individual, the age, sex, and weight of the individual, idiosyncratic responses of the individual, the dosimetry, and the like. Detectably effective amounts of the imaging agent of the present disclosure can also vary according to instrument and digital processing related factors. Optimization of such factors is well within the level of skill in the art.

As used herein, the term "host" or "organism" includes humans and mammals (e.g., mice, rats, pigs, cats, dogs, and horses,). Typical hosts to which compounds of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. The term "living host" refers to host or organisms noted above that are alive and are not dead. The term "living host" refers to the entire host or organism and not just a part excised (e.g., a liver or other organ) from the living host.

As used herein, the term "in vivo imaging" refers to imaging living hosts (e.g., human or mammals).

Discussion

In accordance with the purpose(s) of the present disclosure, as embodied and broadly described herein, embodiments of the present disclosure, in one aspect, relate to methods of imaging a living host using Raman nanoparticles; methods of generating a true image of a living host having been administered Raman nanoparticles; methods of multiplex imaging of a living host using a plurality of Raman nanoparticles; methods of generating multimodality images by combining Raman images with other functional/anatomical images; labeled Raman nanoparticles; and the like. The term "true image" refers to the fact that it is not a single spectral measurement of a small region being performed, but instead a pixel by pixel representation of spectral measurements to form an image of the area of interest. A pixel can be a single point (e.g., area) in a graphic image. For example, 50, 100, 1000, 10,000, 100,000, or more pixels can be in a square inch.

An advantage of imaging a living host is that it allows one to study a biological process of interest (e.g., levels of cancer cell receptors) by forming an image of the biological process. This image is then quantitatively related to the underlying biological process since the color of each pixel in the image represents a quantitative value. Embodiments of the present disclosure set the foundation for developing images of Raman nanoparticle concentration on a pixel-by-pixel basis, which then allows estimation of underlying levels of molecular targets that the Raman nanoparticles are bound to.

The Raman nanoparticles include, but are not limited to, SERS nanoparticles, nanotubes, composite organic inorganic nanoparticles (COINS), and the like. Each of the Raman nanoparticles can include targeting biomolecules (e.g., proteins) so that targeted areas (e.g., organs (e.g., liver), and the like) can be imaged.

The SERS nanoparticle includes, but is not limited to, a core, a reporter compound, and an encapsulant material. The encapsulant material covers and protects the core and reporter compounds. The reporter compounds are attached to the core. The core can be made of materials such as, but not limited to, copper, silver, gold, and combinations thereof, as well as of other metals or metalloids. Different types of SERS nanoparticles can be selected, where each SERS nanoparticle has a different Raman signature. Thus, the use of different SERS nanoparticles enables multiplexing. Additional details regarding the SERS nanoparticles are provided in WO 2006/073439, U.S. Pat. No. 6,514,767, and U.S. Patent Application No. 60/557,729, each of which are incorporated herein by reference as they pertain to the detailed description of each application or patent and as they relate to SERS nanoparticles and SACNs.

In an embodiment, the SERS nanoparticles include Surface Enhanced Spectroscopy-Active Composite Nanoparticles (SACNs). SACNs and methods of making SACNs are described in WO 2006/073439, U.S. Pat. No. 6,514,767, and U.S. Patent Application No. 60/557,729, each of which is incorporated herein by reference as they pertain to the detailed description of each application or patent and as they relate to SACNs. Embodiments of the SACNs can include a SERS nanoparticle, a submonolayer, monolayer, or multilayer of reporter molecules in close proximity to the metal surface, and an encapsulating shell (e.g., a polymer, glass (SiO:), or a other dielectric material). In an embodiment, the reporter compound is disposed at the interface between the SERS nanoparticle and the encapsulant. In an embodiment, a SACN comprises (i) a metal nanoparticle core (e.g., Au or Ag), (ii) a Raman-active reporter (reporter compound), that gives a unique vibrational signature, and (iii) an SiO: encapsulant that "locks" the reporter molecules in place while also providing a highly compatible surface for subsequent immobilization of biomolecules. The glass coating can also stabilize the particles against aggregation and can prevent competitive adsorption of unwanted species. In an embodiment, the SERS nanoparticle comprises polymer coatings adjacent to the nanoparticle.

As used herein, the term "reporter compound" includes Raman-active compounds that produce a unique SERS signature in response to excitation by a laser. In certain embodiments, Raman-active organic compounds are polycyclic aromatic or heteroaromatic compounds. In an embodiment, the reporter compound can include, but is not limited to, 4-mercaptopyridine (4-MP); trans-4,4'bis(pyridyl)ethylene (BPE); quinolinethiol; 4,4'-dipyridyl, 1,4-phenyldiisocyanide; mercaptobenzamidazole; 4-cyanopyridine; 1',3,3,3',3'-hexamethylindotricarbocyanine iodide; 3,3'-diethyltiatricarbocyanine; malachite green isothiocyanate; bis-(pyridyl) acetylenes; Bodipy; TRIT (tetramethyl rhodamine isothiol); NBD (7-nitrobenz-2-oxa-1,3-diazole); Texas Red dye; phthalic acid; terephthalic acid; isophthalic acid; cresyl fast violet; cresyl blue violet; brilliant cresyl blue; para-aminobenzoic acid; erythrosine; biotin; digoxigenin; 5-carboxy-4',5'-dichloro-2',7'-dimethoxy fluorescein; 5-carboxy-2',4',5',7'-tetrachlorofluorescein; 5-carboxyfluorescein; 5-carboxy rhodamine; 6-carboxyrhodamine; 6-carboxyletramethyl amino phthalocyanines; azomethines; cyanines; xanthines; succinylfluoresceins; aminoacridine; fullerenes; organocyanides (e.g., isocyanide), and the like, and combinations thereof.

In an embodiment, the SERS nanoparticle includes nanotubes. Embodiments of the nanotube have an inherent Raman signature that can be detected by the Raman imaging system. The nanotube can be made of materials such as, but not limited to, carbon, and combinations thereof. The nanotubes have a length of about 0.5 to 1000 nm, a diameter of about 2 to 10 nm, and a thickness of about 1 atom layer. One or more of the dimensions of the nanotubes can potentially be adjusted to provide different Raman signatures. Also multi-wall nanotubes (two walls, or three walls, etc.) can be used to provide multiplexing. Thus, the use of various types of nanotubes enables multiplexing.

In an embodiment, the nanotubes include single-wall carbon nanotubes (SWNT). SWNT are fullerenes of closed-cage carbon molecules typically arranged in hexagons and pentagons. (See B. I. Yakobson and R. E. Smalley, American Scientist, Vol. 85, July-August, 1997, pp. 324-337, which is incorporated herein by reference). In an embodiment, the single-wall carbon nanotubes may have diameters from about 0.6 nanometers (nm) up to about 3 nm, about 5 nm, about 10 nm, about 30 nm, about 60 nm or about 100 nm. In an embodiment, the single-wall carbon nanotubes may have a length from about 50 nm up to about 1 millimeter (mm), or greater. In an embodiment, the diameter of the single-wall carbon nanotube is about 2 to 5 nm and has a length of about 50 to 500 nm.

A COIN includes several fused or aggregated primary metal crystal particles with the Raman-active organic compounds (reporter compound) adsorbed on the surface, within the junctions of the primary particles, or embedded in the crystal lattice of the primary metal particles. The primary metal crystal particles are about 15 nm to 30 nm, while the fused or aggregated COIN is about 50 nm to about 200 nm. The primary metal crystal particle is made of materials such as, but not limited to, gold, silver, platinum copper aluminum, and the like. The Raman-active organic compound refers to an organic molecule that produces a unique SERS signature in response to excitation by a laser. Additional details regarding COINs are described in U.S. Patent Applications 20050142567, 20060234248, and 20070048746, each of which is incorporated herein by reference for the corresponding discussion.

COINs can also serve as Raman nanoparticles to provide imaging signals. The COINs can be functionalized so they have better solubility in blood and can target potential targets in a living subject. Multiple COINs can be used as with other Raman nanoparticles in order to provide multiplexing of signals.

In an embodiment, the Raman nanoparticle can include a chemical or biological compound having an affinity for a target in the living host. In particular, the Raman nanoparticle can include, but is not limited to, a drug, a therapeutic agent, a radiological agent, a chemological agent, a small molecule drug, a biological agent (e.g., peptides, proteins, antibodies, antigens, and the like) and combinations thereof, that can be used to image, detect, study, monitor, evaluate, and/or screen a disease, condition, or related biological event corresponding to the target. It should be noted that Raman nanoparticle modified with conjugation to other molecules (e.g., proteins, peptides, small molecules, and the like) in order to target the nanoparticle to a particular molecular target are intended to be covered by embodiments of the present disclosure. For example, a nanotube can be modified with RGD peptide so that it can target new blood vessels in tumors and would allow detection of tumor by imaging with a Raman imaging system.

Embodiments of the present disclosure include Raman nanoparticles that can be used to image, detect, study, monitor, evaluate, and/or screen a living host (e.g., whole-body or a portion thereof) or an agent given to the living host (e.g. human, rat, mouse, and the like). In particular, embodiments of the present disclosure include Raman nanoparticles that can be used to non-invasively image deep tissue (e.g., up to about 5-10 cm) in a living host using Raman spectroscopy. The Raman nanoparticle can be imaged using a Raman imaging system, which is described in detail in the examples. The Raman imaging system is capable of creating an image of a living host, which is in contrast to just measuring a signal in a host.

In particular, a living host is administered one or more Raman nanoparticles. The living host and the Raman imaging system are positioned so that the Raman imaging system can perform a scan (e.g., raster scan) of a portion of the host or the entire host to obtain a point-by-point Raman image (e.g., mapping) of the living host. The Raman imaging system can include or be near one or more components to provide anesthesia or other medical assistance to sustain the living host. Scanning the host using the Raman imaging system produces a true Raman image or map of the host that illustrates in a point-by-point fashion the Raman signal present in the host. The Raman image is a two-dimensional Raman signal map or image of the living host. A Raman image is different from a bulk signal in that the Raman image is a visual representation of signal as a function of location (e.g., a particular location in the host such as a part (e.g., a few millimeters, a centimeter or more) of the liver, heart, colon, or the like). For example, the Raman signal from the liver is different than a Raman image obtained by scanning the liver in a raster fashion to obtain multiple signals as a function of space and then visually displaying these where an image represents the signal as a function of spatial coordinates of the liver. For example, one could just obtain a bulk signal from the entire liver (a spectra representing the Raman shift). In embodiments of the present disclosure, measurements can be made of multiple spectra based on a raster scan over the liver or any other region, and then an image can be created that represents the point-by-point measurements of many spectra to provide quantitative information on a pixel by pixel basis as opposed to just a bulk signal. Additional details are provided in the Examples.

Embodiments of the present disclosure include administering or otherwise introducing one or more types of Raman nanoparticles (e.g., have emissions at different wavelengths, or two different types of SERS nanoparticles having different metals, or SERS nanoparticles and nanotubes, or the like) to a living host. In embodiments including two or more different types of Raman nanoparticles, each of the Raman nanoparticles has a different Raman signature and/or can be directed to different biological targets. The living host can be imaged using a Raman imaging system. The Raman imaging system is capable of creating an image of a living host, where the Raman image includes signals from each of the different types of Raman nanoparticles administered to the living host. In an embodiment, the different Raman nanoparticles could be used to image different portions (e.g., tissue, cells, organs, and the like) of the living host.

In another embodiment, each of the different Raman nanoparticles could be directed to (e.g., include an agent having an affinity for a particular target) different biological targets relating to the same disease, condition, or related biological event. In this embodiment, the different types of Raman nanoparticles could be used to determine the presence or absence of one or more features of the disease, condition, or related biological event, which is useful for certain cancers (e.g., the type or severity of a cancer can be determined by the presence of one or two targets, and treatment is based on the type or severity of the cancer). Embodiments of the present disclosure include other ways in which a combination of Raman nanoparticles could be used in Raman imaging. Additional details are provided in the Examples.

In another embodiment of the present disclosure, the Raman image can be combined with an anatomical image and/or a functional image of the same living host generated from an anatomical imaging system. The anatomical imaging system can include, but is not limited to, computer topography (CT), ultrasound, magnetic resonance imaging (MRI), and the like. The Raman image can be fused with or otherwise combined with the anatomical image to produce a multimodality image that illustrates the location of the Raman signal relative anatomical features of the living host. In an embodiment, the two images are overlaid so that the Raman signal corresponds to the relative anatomical position of the living host. For example, a Raman image could be combined with an ultrasound image or with a CT image. In addition a Raman image could be combined with a functional image such as positron emission tomography (PET). The combination of multiple functional images or a functional image with an anatomical image would provide more useful information about the exact location of a specific molecular event. The anatomy would tell us where, and the molecular image (functional image) would tell us how much molecular signal from a given anatomical coordinate.

It should be noted that the amount effective to result in uptake of a Raman nanoparticle into the cells or tissue of the living host depends upon a variety of factors, including for example, the age, body weight, general health, sex, and diet of the host; the time of administration; the route of administration; the rate of excretion of the specific compound employed; the duration of the treatment; the existence of other drugs used in combination or coincidental with the specific composition employed; and like factors well known in the medical arts.

Kits

The present disclosure also provides packaged pharmaceutical compositions comprising a pharmaceutically acceptable carrier and one or more Raman nanoparticles of the disclosure. Other packaged pharmaceutical compositions provided by the present disclosure further include indicia including at least one of: instructions for using the Raman nanoparticle to image a living host.

This disclosure encompasses kits that include, but are not limited to, Raman nanoparticles and directions (written instructions for their use). The Raman nanoparticle can be tailored to the particular biological event to be monitored as described herein. The kit can further include appropriate buffers and reagents known in the art for administering the Raman nanoparticle to the living host. The Raman nanoparticle and carrier may be provided in solution or in lyophilized form. When Raman nanoparticle and carrier of the kit are in lyophilized form, the kit may optionally contain a sterile and physiologically acceptable reconstitution medium such as water, saline, buffered saline, and the like.

EXAMPLES

Now having described the embodiments of the present disclosure, in general, examples 1-3 describe some additional embodiments of the present disclosure. While embodiments of the present disclosure are described in connection with examples 1-3 and the corresponding text and figures, there is no intent to limit embodiments of the present disclosure to these descriptions. On the contrary, the intent is to cover all alternatives, modifications, and equivalents included within the spirit and scope of embodiments of the present disclosure.

Example 1

Introduction

Molecular imaging of living subjects continues to rapidly evolve with bioluminescence and fluorescence strategies, in particular, being frequently utilized for small animal models. This example discusses embodiments of the first non-invasive deep tissue molecular images in a living subject with the use of Raman spectroscopy. We describe a novel strategy for small animal optical imaging based on Raman spectroscopy and Raman nanoparticles. Surface-enhanced Raman scattering (SERS) nanoparticles (namely, Nanoplex™ Biotags (Oxonica Inc, Mountain View, Calif.) were used in this study and henceforth referred to as SERS-biotags or biotags) and single wall carbon nanotubes (SWNT) were utilized to demonstrate whole-body deep tissue Raman imaging, nanoparticle pharmacokinetics, multiplexing, and in vivo tumor targeting after tail-vein injection, using an imaging system adapted for small animal Raman imaging. The novel imaging modality reported here holds significant potential as a new strategy for biomedical imaging of living subjects.

Results

Optimization of Raman Imaging Instrumentation

Optical microscopes designed for surface imaging through transparent media face significant losses of light when imaging through a diffusive tissue due to light scattering. We utilized a Raman imaging setup based on a Renishaw In Via Raman microscope (Renishaw plc, New Mills, UK) equipped with an excitation laser at 785 nm which is typically employed for surface imaging. Several measures were taken to optimize this setup specifically for small animal imaging. A high numerical aperture (NA) objective, commonly used on this microscope setup, was found to be less than ideal when imaging small animals for both illumination and light collection. A small spot size illumination obtained by a high NA objective limits the permissible laser power that can be used before tissue damage. Moreover, high NA objectives collect light efficiently only from a small spot size; a highly diffusive propagation of light photons through tissue results in only a very small number of scattered photons emanating from the same small spot size. For these reasons we found that a 12× open field lens with a defocused beam resulting in a spot size of 20×200 µm worked well. The spectral resolution was adjusted to allow high sensitivity while at the same time being able to multiplex different SERS nanoparticles by opening the monochromator slit (100 µm width) to obtain a spectral resolution of 10 cm$^{-1}$. A computer controlled stage was also added to the microscope setup to allow automated mapping of large surfaces. Raman images were obtained by using a Raman point mapping method. The computer-controlled x-y translation stage performed a raster scan of a region of interest over the mouse, the Raman spectrum was measured at every point and software algorithms were used to calculate the SERS nanoparticle concentration and generate a two-dimensional mapping image of the SERS nanoparticle distribution. Finally, a heated bed and an anesthesia inhalation unit were attached to the microscope stage to allow a long, motionless scan time at a stabilized body temperature. A photograph of the imaging setup is shown in the section below noted below and in FIG. 1-5(*a*).

Raman Nanoparticles

The ideal properties of a nanoparticle used for small animal Raman spectroscopy would include small dimensions, simple conjugation methods, no toxicity effects and intense and unique Raman spectra. Recently developed SERS active nanoparticles, called Nanoplex™ Biotags (Oxonica Inc., Mountain View, Calif.), composed of a gold core, Raman-active molecular layer (see methods) and silica coating, schematically shown in FIG. 1-5(*b*), hold significant potential for in vivo imaging applications (see, *Langmuir* 19, 4784-4790, which is incorporated herein by reference for the corresponding discussion). The glass coating of these SERS nanoparticles guarantees physical robustness, insensitivity to environmental conditions, and simple biofunctionalization of the well studied silica surface chemistry. The SERS-nanoparticles were designed to maximize the Raman signal and the NIR excitation and emission profiles are ideal for minimizing light absorption by tissue. SERS nanoparticles used in this study had a mean diameter of 120 nm as seen in the transmission electron microscopy image in FIG. 1-6.

SWNT exhibit a strong Raman peak at 1593 cm$^{-1}$ which allows high sensitivity detection (FIG. 1-7). Unlike the SERS nanoparticles, these SWNTs are inherently Raman active and don't use a metal surface enhancer to increase Raman detection. The high aspect ratio of the carbon structure of SWNTs is ideal for bio-conjugation and recent reports have successfully shown specific tumor targeting in-vivo within various tumor models using various functionalized SWNTs (see, *Nature Nanotech* 2, 47-52, *J Nucl Med* 48, 1180-9, and *Gene Ther* 13, 1714-23, each of which is incorporated herein by reference for the corresponding discussion). SWNTs have a very small diameter of ~3 nm and a length of 200 nm, as schematically shown in FIG. 1-5(*c*) and on the atomic force microscopy image in FIG. 1-6(*b*). SERS and SWNT nanoparticles were both tested for stability in mouse serum and incubated at 37° C. over a 5 day period with no degradation of Raman signal detected (data not shown).

Imaging System Characterization

We demonstrated the in vitro and in vivo reproducibility of the measured and processed Raman spectra. Five samples (5 µl volume) each with 6.6 fmol of SERS nanoparticles were measured on a piece of parafilm using the Raman imaging setup. The coefficient of variance (COV) of the calculated SERS nanoparticle concentration using the quantitative analysis method described later (see methods) showed a reproducibility of 1.9%. Reproducibility was also evaluated in a nude mouse with 4 separate subcutaneous injections of 16 fmol SERS nanoparticle (10 µl volume) mixed with a gelatinous protein mixture known as matrigel which resembles the complex extracellular environment found in many tissues (10 µl volume). The matrigel was used to keep the SERS nanoparticles from diffusing quickly out of the skin, and showed no inherent Raman spectra as expected (FIG. 1-8). The SERS nanoparticle component concentration calculated for different injection sites showed a COV of 3.1%. Deep tissue reproducibility was also determined by injecting 260 fmol of SERS nanoparticles (200 µl volume) via tail-vein into three nude mice. Nanoparticles of various types are naturally taken up by the reticuloendothelial system and thus can be found in the Kupffer cells of the liver. The liver of each mouse was imaged approximately 30 minutes post tail-vein injection and component analysis revealed a COV of 16.7% between the three mice. Naturally, the higher variability could be attributed to a number of factors, such as positioning, injection technique, and individual animal pharmacokinetics. Reproducibility in the liver of a single mouse imaged repeatedly (8 times) showed a COV of 2.8% (data not shown).

Sensitivity was evaluated by subcutaneously injecting three mice with decreasing concentrations of SERS nanoparticles in a volume of 20 µl. The data revealed a highly linear relationship between calculated and injected concentration of nanoparticles with an $R^2=0.99$. The smallest amount of SERS nanoparticles detected in a 20 µl subcutaneous injection was 8.125 pM. Ex-vivo measurements showed high linearity with $R^2=0.997$ and detection limit as low as 600 particles (FIG. 1-9).

The maximum depth of penetration for our Raman microscope was evaluated using a tissue mimicking phantom where a maximum depth of 2 mm was observed using 6 nM SWNTs and 5.5 mm using 1.3 nM SERS nanoparticles (more details in SI Text below).

The effect of changing the working distance between the lens and the subject was also evaluated ex-vivo, by changing the stage height that contained a 5 µl sample of 6.6 fmol SERS nanoparticles and in-vivo with a mouse that had been injected via tail vein, with a 200 µl sample of 260 fmol SERS nanoparticles. The component concentration was found to increase exponentially as the sample/mouse on the stage was moved closer to the lens of the microscope (data not shown). However, calculated concentration is only weakly dependent on variations in objective-subject distance when detected through the diffusive mouse tissue.

Demonstration of SERS Nanoparticle Multiplexing in Mice

Each type of the SERS nanoparticles (Nanoplex™ biotags) contains a different Raman-active material with its own unique spectral fingerprint allowing detection and quantification of multiple tags simultaneously within the same animal. Two types, SERS 421 and SERS 440, with different Raman signatures were subcutaneously injected into a mouse to demonstrate the multiplexing capabilities in living subjects. The first subcutaneous injection consisted of 5 µl (6.6 fmol) of S421 and 15 µl of matrigel (FIG. 1-1a). The second subcutaneous injection consisted of 5 µl (6.6 fmol) of SERS 440 and 15 µl of matrigel (FIG. 1-1b). The third subcutaneous injection consisted of an equal mix of SERS 421 (5 µl), SERS 440 (5 µl) and 10 µl matrigel (FIG. 1-1c). Based on their different Raman spectra, the concentration of each SERS nanoparticle could be calculated using the component analysis method described later (see methods). FIG. 1-1 shows the concentration mapping of the injection sites. The area of the three subcutaneous injections was mapped with a step size of 500 µm and an integration time of 1 second. The map shows the three individual injection sites; each assigned a color by the Nanoplex™ software based on their corresponding spectra, with the concentration magnitude portrayed as pixel brightness. Notice the third injection site was calculated to have a yellow color which correlates with an equal mix of the SERS 421 (assigned red) and SERS 440 (assigned green) SERS nanoparticles. Ex-vivo experiments verifying the system's multiplexing capability are shown in FIG. 1-10.

Figures 1, 2:
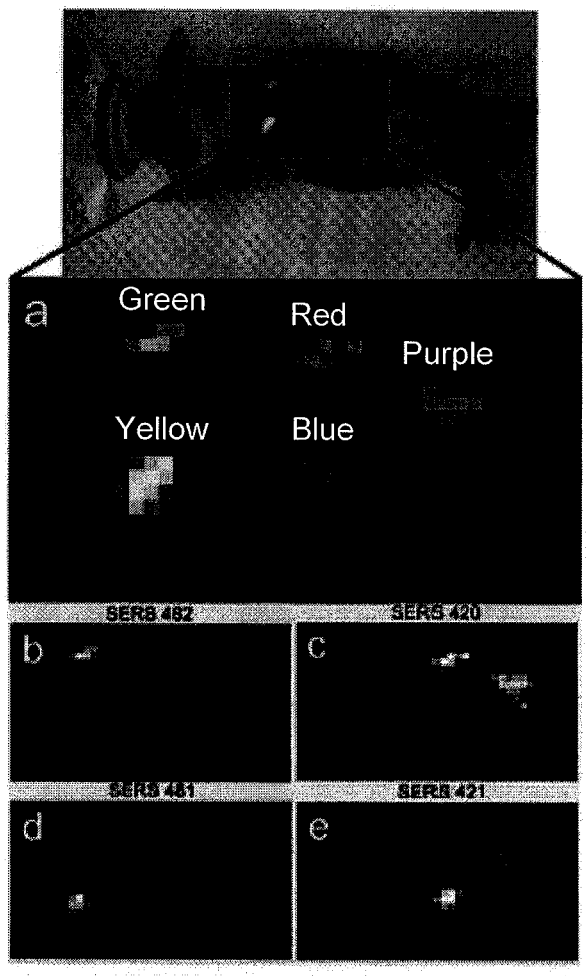

In addition, we have been able to successfully multiplex 4 types of SERS Raman nanoparticles of varying concentrations in a living mouse. The first four subcutaneous injections consisted of 5 µl (6.6 fmol) of each SERS particle and 5 µl of matrigel as shown in FIG. 1-2(a) as follows: SERS 482 (assigned green), SERS 420 (assigned red), SERS 481 (assigned yellow) and SERS 421 (assigned blue). The fifth subcutaneous injection (assigned purple) at the far right consisted of a mixture of these four SERS particles with varying concentrations to determine multiplexing in-vivo (FIG. 1-2(a)). The mixture contained 4 µl of SERS 420 (5.28 fmol), 3 µl of SERS 421 (3.96 fmol), 2 µl of SERS 481 (2.64 fmol) and 1 µl of SERS 482 (1.32 fmol) and 10 µl matrigel. Based on their different Raman spectra, the concentration of each SERS nanoparticle could be calculated using the component analysis method. FIGS. 1-2(b) to 1-2(e) show the four SERS components and the correlating intensity of the fifth injection site corresponding to the concentration of that particular component. The different intensities of the fifth injection site represented in each of the maps (FIGS. 1-2(b) to 1-2(e)) qualitatively correlates with the different concentrations of each SERS nanoparticle mixed. Notice how SERS 420 has the most intense pixel brightness in the fifth injection site (FIG. 1-2(c)), followed by SERS 421 (FIG. 1-2(e)) with the second most intense, then SERS 481 with the third most intense (FIG. 1-2(d)) and finally SERS 482 with the least intense pixel brightness at the fifth injection site (FIG. 1-2(b)). The area of the five subcutaneous injections was mapped with a step size of 750 µm and an integration time of 1 second. The map shows the five individual injection sites; each assigned a color by the software based on their corresponding spectra, with the concentration magnitude portrayed as pixel brightness. The unique Raman spectra of each of these four different SERS nanoparticle are depicted in FIG. 1-12.

Liver Pharmacokinetics of SERS Nanoparticles and SWNTs

Taking advantage of the multiplexing capabilities of SERS nanoparticles detected by Raman spectroscopy, we studied the circulation properties of both pegylated and non-pegylated SERS nanoparticles simultaneously in living mice. An equal mixture of pegylated (PEG) and non-pegylated SERS nanoparticles (260 fmol in 200 µl volume), each with different Raman signatures, were tail-vein injected to evaluate their accumulation in the liver as a function of time. The laser was positioned over the mouse's liver before injection and a Raman spectrum was acquired with a 10 second integration time over 90 minutes. Quantitative analysis was used to calculate the relative concentration of the two different SERS nanoparticles, which nearly simultaneously accumulated in the liver (FIG. 1-13). The first group of mice (n=3) that received an equal mix of 5 kD PEG and non-pegylated SERS nanoparticles showed no difference in liver accumulation between each of the nanoparticles and at 2 minutes post-injection (FIG. 1-3a). The second group of mice (n=3) that received an equal mix of 20 kD PEG and non-pegylated SERS nanoparticles also showed no difference in liver accumulation between each of the nanoparticles and plateaued at 4 minutes post-injection (FIG. 1-3b). As with many nanoparticles administered intravenously, evading the macrophages of the reticuloendothelial system remains a constant problem, where in some in-vivo cases pegylation is insufficient, as seen in our data and reported by others. The pharmacokinetics of SWNTs were also evaluated over 90 minutes in 4 mice to reveal a fluctuation in nanotube distribution in the liver over the first 10 minutes followed by a continuous increase out to 90 minutes (FIG. 1-3c).

Whole-body Noninvasive Imaging of SERS Nanoparticles

For whole-body mapping, mice were tail-vein injected with 260 fmol of SERS nanoparticles in a 200 µl volume. A raster scan was acquired 2 hours post-injection over a large portion of the mouse body with 1 mm step size and 3 second integration time. Quantitative analysis software calculated the concentration of SERS nanoparticles and generated an image showing accumulation of the SERS nanoparticles in the liver (FIG. 1-4a). A finer mapping with step size of 750 µm over the liver region reveals a detailed image of the liver. A slight distinction between liver lobes can be seen in this higher resolution image (FIG. 1-4b). SERS nanoparticles were visualized in the liver region out to 24 days post tail-vein injection, and continued to produce a recognizable spectrum with sustainable intensity for 24 days. Sacrificed animals with ex vivo tissue analysis confirmed the presence of SERS nanoparticles in the liver of mice (data not shown).

Whole-body Noninvasive Imaging and Tumor Targeting of SWNTs

SWNTs were also imaged in nude mice after tail-vein injection of approximately 60 pmol in 200 µl intense peak at 1593 cm$^{-1}$ makes nanotubes easily detected with Raman spectroscopy. A Raman image was acquired with a raster scan 2 hours post-injection with a step size of 1 mm and an integration time of 3 seconds. The map revealed accumulation of nanotubes in the liver as well as a random distribution faintly dispersed across the peritoneal cavity (FIG. 1-14(a)). The SWNTs were also evaluated daily for liver accumulation and showed an increase in Raman intensity several days after tail-vein injection. Due to this continuous rise in Raman signal in the liver, another map of the same area, using the same image acquisition parameters, was taken at 72 hours post-injection to reveal a better defined liver with better delineation of the liver than the previous 2 hour image of the same area (FIG. 1-14(b)). Daily evaluation of the liver continued to show Raman signal in the liver, out to 12 days post injection at which time the animals were sacrificed. Sacrificed animals with ex vivo tissue analysis confirm the presence of nanotubes in the liver of mice (data not shown).

Furthermore, preliminary data demonstrated the ability of our modified Raman microscope to detect targeting of SWNTs conjugated with arginine-glycine-aspartate (RGD) peptide in an integrin positive U87MG tumor model in living mice. This RGD peptide binds to $\alpha_v\beta_3$ integrin which is overexpressed in angiogenic vessels and various tumor cells (see, Curr Pharm Des 12, 2723-47, which is incorporated herein by reference for the corresponding discussion). Tumor targeting of RGD SWNTs was previously described by Liu et al (see, Nature Nanotech 2, 47-52, which is incorporated herein by reference for the corresponding discussion) using microPET imaging and ex-vivo Raman imaging of tissues. Six mice, subcutaneously inoculated with 20 million U87MG cells near the right shoulder were divided into two groups. The first group (experimental) received a tail-vein injection of RGD conjugated SWNTs of approximately 60 pmol in 200 µl. The second group (control) received an intravenous injection of plain non-targeted SWNTs of the same concentration. Raster scans were acquired at 24 hours post SWNT injection over the tumor area with 750 micron steps to generate Raman images (FIG. 1-4a). The images revealed an intense accumulation of RGD conjugated SWNTs in the tumor area, however little to no accumulation of plain SWNTs was observed in the tumor area at 24 hours post injection. Raman spectra were taken in living mice at 24 hours post-injection and revealed a significant increase (p<0.05) in SWNT accumulation in the tumor areas of experimental mice receiving RGD SWNTs (SWNT concentration: 0.0204±0.0087) as compared to the control group receiving plain SWNTs (SWNT concentration: 0.0016±0.0005) (FIG. 1-4b).

Discussion

In summary, embodiments of the present disclosure were adapted a Raman microscope to demonstrate Raman imaging of small living subjects while utilizing two different types of Raman nanoparticles, SERS active nanoparticles (Nanoplex™ Biotags) and SWNT. We have shown relatively high signal reproducibility both in vitro and in living subjects and the ability to produce an image of nanoparticles from both subcutaneous locations, as well as from deeper tissues (e.g., liver) in living mice. Furthermore, we have demonstrated the ability to follow the arrival of nanoparticles in liver tissue to create time-activity curves. A minimum detection sensitivity of 8.125 pM was observed in a living mouse while using SERS nanoparticles. The ability to multiplex with four SERS nanoparticles presenting different Raman spectra was also demonstrated with the rapid and straightforward distinction between these nanoparticles in living mice. These initial results are encouraging and demonstrate the potential robustness of a Raman-based imaging strategy for small living subjects.

In this example we demonstrated detection of Raman nanoparticles in both superficial and deep tissues along with an initial evaluation of its potential to detect tumor targeting with SWNTs conjugated to RGD peptide in an U87MG animal model. The primary limitation to Raman imaging of larger subjects will be those also faced by other optical techniques and is limited by NIR light penetration beyond a few centimeters of tissue (see, Molecular imaging 3, 9-23, which is incorporated herein by reference for the corresponding discussion). The key advantages of the current Raman imaging strategy over fluorescence is the very high multiplexing capability and lack of confounding background signal from autofluorescence. A paper by Souza et. al., was able to collect a Raman spectra from the surface of a mouse (without forming any images) but had to use intratumoral injection of nanoparticles and also a very large concentration (3.8 µM) of Raman nanoparticles in a relatively large volume of 300 µl (see, Anal Chem 78, 6232-7, which is incorporated herein by reference for the corresponding discussion). Another group has applied multiple Raman signals to follow the distribution of cholesterol in a rat eye while simultaneously showing the phenotyping of lymphocytes by using a single non-enhanced Raman-labeled (filipin) polystyrene bead to monitor cholesterol in a rat eye in conjunction with the inherent Raman peak associated with proteins to follow the distribution of cholesterol (see, Appl Spec 50, 545-551, which is incorporated herein by reference for the corresponding discussion). Furthermore, it was shown that these Raman labeled polystyrene spheres could be successfully used in combination with a fluorescent label. Using an additional Raman label, can overcome the many limitations that arise with fluorescence such as photobleaching, autofluorescence and limited number of fluorescent labels. Although we demonstrated multiplexing with only four SERS nanoparticles, we should be able to image many more simultaneously injected SERS nanoparticles, and as many as 10 spectrally distinct SERS nanoparticles are already available (e.g., Oxonica Inc.).

Glass-encapsulated SERS active nanoparticles are only one kind of Raman particle recently developed that can be employed as contrast agents for molecular imaging. Roughened surface noble metal nanoparticles labeled with binding affinity molecules have also been shown to dramatically increase the Raman signal of their complementary molecules once attached through the SERS mechanism (see, Langmuir 19, 4784-4790,. J. Raman Spectrosc 36, 485-496, and, Anal Chem 77, 6147-54, each of which is incorporated herein by reference for the corresponding discussion). Conjugation of monoclonal antibodies with SERS nanoparticles for targeting and imaging of specific cancer markers in live cultured cells was also recently investigated (see, Anal Chem 79, 916-22, which is incorporated herein by reference for the corresponding discussion). Another study presents the first in vivo application of SERS for glucose measurements in a rat (see, Anal Chem 78, 7211-5, which is incorporated herein by reference for the corresponding discussion) by subcutaneous implantation of functionalized SERS nanospheres.

Recent publications have reviewed the rapid increase of Raman spectroscopy in many biomedical applications (see, Biopolymers 67, 1-9, Biotechnol Annu Rev 11, 191-225, and Phys Med Biol 45, R1-59, each of which is incorporated herein by reference for the corresponding discussion). One report has demonstrated the ability of Raman spectroscopy to diagnose benign and malignant excised breast tissue with high sensitivity and specificity (see, Proc Natl Acad Sci USA 102, 12371-6, which is incorporated herein by reference for the corresponding discussion). Another paper discusses the potential of Raman spectroscopy to analyze the morphologic composition of atherosclerotic coronary artery lesions and assess plaque instability and disease progression in vivo (see, Cardiovasc Pathol 10, 59-68, which is incorporated herein by reference for the corresponding discussion). The recent development of a highly efficient Raman optical fiber probe has now bridged the gap between Raman spectroscopy and the clinical setting. The optical fiber probe has successfully demonstrated its usefulness in assessing human tissue models for disease and thus has great potential as a clinically practical technique (see, Appl Opt 43, 542-54 and J Biomed Opt 10, 031113, each of which is incorporated herein by reference for the corresponding discussion). In particular, this Raman optical fiber probe has the potential of being an extremely useful tool in an intraoperative setting, for instance in surgical debulking of cancers. Its ultra high sensitivity would be useful in detecting even the smallest presence of malignant tissues in the human body for excision. Utilizing targeted SERS nanoparticles and noninvasive in vivo imaging, as demonstrated in this paper, supports that Raman spectroscopy can become an important clinical diagnostic tool.

Biodistribution of these Raman nanoparticles are currently being evaluated in our lab with the use of radiolabels (e.g., with positron emitters) so that quantification of exact nanoparticle concentration can be explored, as we have recently done with radiolabeled quantum dots (see, J Nucl Med 48, 1511-1518, which is incorporated herein by reference for the corresponding discussion). Additional work with tissue targeting of the Raman nanoparticles (SERS and SWNT) should also help to further expand the eventual utility of the strategies developed in this work. Further studies with both SERS and SWNT will still be needed to understand any potential limitations including delivery due to nanoparticle size, optimal injected dose, and potential for toxicity. Just as quantum dots are finding increasing applications for imaging of small animal models so should Raman nanoparticles lead to increasing applications without the limitations faced by conventional fluorescence imaging. Furthermore, the high sensitivity associated with our modified Raman microscope in conjunction with SERS nanoparticles (8.125 pM) represents an important advantage over the sensitivity of conventional fluoroscopy imaging devices in conjunction with quantum dots (~11 nM using IVIS (Xenogen Corp., Hopkinton, Mass.) and Maestro (CRi Inc., Woburn, Mass.) imaging systems (unpublished data)). Additional comparisons between quantum dots and Raman nanoparticles should help to further demonstrate the true advantages of each technique. Although no single molecular imaging strategy (including Raman) is optimal for all biological models, the use of the current Raman imaging strategy along with existing optical and non-optical strategies should help continue to expand the available tool-box for the field of molecular imaging. In addition, we are currently developing new Raman spectroscopy instrumentation for dedicated imaging of small living subjects and this should lead to faster image acquisition times and potential for estimation of signal depth and eventual tomographic imaging. Further optimized instrumentation and more studies with various Raman nanoparticles should help to markedly expand the use of Raman imaging of small living subjects and should also impact newer clinical imaging strategies. The current work sets the foundation for future studies and supports continued investigation of Raman imaging of living subjects.

Methods

Raman imaging setup. The Renishaw InVia Raman microscope, shown in FIG. 1-5, consisted of a semiconductor diode near-infrared laser operating at 785 nm delivering 60 mW to the sample. Light was guided through a collimator onto a series of mirrors which focused the light through an open field 12× microscope lens. The mouse was illuminated with the laser beam. Light from the illuminated spot was collected with a lens and sent through a monochromator. Rayleigh scattering close to the laser line was filtered through an edge filter. The remaining inelastic (Raman) scattered light was then focused through a slit (100 μm width) and dispersed by a diffraction grating (600 grooves/mm) onto a CCD detector (deep depletion, PE-cooled to −70 C, with a size of 576 by 384 pixels, each pixel size is 22 by 22 μm) which then sends the detected Raman spectra to a workstation for further processing.

SERS and SWNT nanoparticles. SERS active nanoparticles, Nanoplex™ Biotags, were provided by Oxonica Inc. (Mountain View, Calif.) which consisted of gold nanoparticles covered with a layer of Raman-active material and coated with glass. For more details on the structures of these SERS nanoparticles please see SI Text below and FIG. 1-15. The SWNT were provided courtesy of Dr. Hongjie Dai (Stanford University) and had dimensions of a few nanometers in diameter and approximately 200 nm in length (FIG. 1-5(c)).

Animal experiments. Female 8 week old nude mice (Charles River) were used for all Raman spectroscope studies. All procedures performed on the animals were approved by the Stanford University Institutional Animal Care and Use Committee, and were within the guidelines of humane care of laboratory animals.

Animal injections. Four mice were subcutaneously injected with 13 fmol of SERS nanoparticles in a 20 μl volume using a 26 gauge needle. Four separate mice were injected via tail-vein with 260 fmol of SERS nanoparticles in a 200 μl volume using a 26 gauge needle. Four additional mice were injected via tail-vein with 60 pmol of SWNTs in a 200 μl volume using a 26 gauge needle.

Mouse Tumor Model. U87MG human glioblastoma (American Type Culture Collection, ATCC) were cultured under standard conditions. The U87MG tumor models were generated by a subcutaneous injection of 20×10$^6$ cells in 200 μl PBS near the right shoulder of the mice. Six female nude mice were inoculated with a subcutaneous injection near the right shoulder. When the tumor volume reached approximately 200 mm$^3$, three mice were tail-vein injected with RGD SWNTs (experimental group) and three mice were injected with plain SWNTs (control group). In-vivo Raman spectroscopic measurements were taken of the tumor site in living mice 24 hours post IV injection to evaluate accumulation of RGD versus plain SWNTs in the tumor.

Preparation and Conjugation of Pegylated SWNTs with RGD. Single wall nanotubes were prepared as described by Liu et. al., due to space constraints detailed description of RGD chemistry conjugation is provided elsewhere (see, *Nature Nanotech* 2, 47-52, which is incorporated herein by reference for the corresponding discussion). The SWNT were provided by Dr. Hongjie Dai (Stanford University) and have dimensions of a few nanometers in diameter and approximately 200 nm in length yielding a concentration of 300 nM and a molecular weight of 170 kDa.

Raman spectroscopic imaging in living mice. Raman measurements were performed with a Renishaw microscope system. A semiconductor diode near-infrared laser operating at λ=785 nm was used as the excitation source with a laser power of 60 mW measured at the surface of the mouse's skin (ANSI exposure limits in SI Text below). Raman images were obtained by using a Raman point mapping method. A computer-controlled x-y translation stage was used to raster-scan the mouse, creating a spectral image by measuring the Raman spectrum of each individual pixel in the area of interest with a 500 μm, 750 μm or 1 mm step size. Integration times of 3 seconds per step were used to acquire our Raman maps (see SI Text below for more details on integration times). The objective lens used was a 12× open field in a dimly lit room.

Quantitative spectral analysis. The direct classical least squares (DCLS) method, also called linear un-mixing and K-matrix methods, was used in this work to perform a quantitative analysis of Raman spectroscopy (see, *Appl Spec* 34, 539-548 and *Appl Spect* 57, 20A-42A, each of which is incorporated herein by reference for the corresponding discussion). More details are provided in SI Text below.

Supplemental Information for Example 1
Depth of Penetration Phantom Study.

The maximum depth of penetration for SWNTs and SERS nanoparticles was determined using a tissue mimicking phantom. The phantom was prepared using a combination of agar, lipid, distilled water and India Ink with an absorbance of 17.36 at 785 nm. An inclusion was made in the agar phantom and filled with a known concentration of either SERS or SWNTs. The phantom was then filled at 0.5 mm depth increments and imaged with the Raman microscope at each depth. It was determined that the maximum depth of penetration was 2 mm for a 6 nM concentration (estimated accumulation in tumor volume) of SWNTs in a 200 mm$^3$ volume (equivalent to tumor volume). It was also determined that the maximum depth of penetration for SERS particles was 5.5 mm for a 1.3 nM concentration in a 200 μl volume (equivalent to IV injection). Note that these depths would increase with increased nanoparticle concentration administration, but were determined as such to satisfy our experimental settings.

SERS and SWNT NanoparticlesNanoparticles.

The Raman active material varied for each of the four SERS particles used in this study and their chemical composition is shown in FIG. 1-15. Note that the molecular vibration of these different chemical bonds after laser excitation is what gives them their unique spectral fingerprint. The dimensions and uniformity of SERS nanoparticles evaluated using transmission electron microscopy (FIG. 1-6) shows an outer glass diameter of 120 nm and gold core diameter of 50 nm. A variety of SERS nanoparticles with different Raman signatures were used in this study. The SERS particles surface chemistry consisted of thiol groups that were introduced into the silica shell using 3-mercaptopropyltrimethoxysilane (MPTMS) and sulfhydrile groups were introduced as similarly described by others. The thiolated SERS were conjugated with malemide activated mPEGs where the maleimide group reacts with thiols on the SERS surface at a neutral pH. The identity of each SERS nanoparticle was determined by its unique Raman spectrum. The SWNT were provided courtesy of Dr. Hongjie Dai (Stanford University) and had dimensions of a few nanometers in diameter and approximately 200 nm in length (FIG. 1-5(*c*)).

Maximum Permissible Exposure.

The power delivered to the mouse's skin was measured to be 60 mW instead of the 100 mW that was reported from the manufacturer. This decrease in power was due to the collimation and filters that the laser passes through before exiting the 12× objective lens and onto the mouse's skin. The area illuminated on the mouse used to acquire raster scan images was approximately 5 mm×10 mm to avoid over exposure to the skin and to collect as many photons as possible. Therefore it was calculated that our laser operated at 0.12 W/cm$^2$. The maximum permissible exposure (reported by ANSI limits) for skin is 0.2958 W/cm$^2$ for a 785 nm laser with an exposure duration time from 10 s to 8 hrs. The maximum permissible exposure for a 3 second acquisition time was 0.713 W/cm$^2$. In both instances where we took 10 second single spot acquisitions or 3 second mapped acquisitions we were under the suggested ANSI MPE limits. In addition, mice revealed no apparent skin burns when monitored for several days post laser exposure.

Deep Tissue Acquisition Integration Time.

The optimal integration time used to acquire the depth of penetration information took no longer than 10 seconds in our phantom study. Integration times as long as 90 seconds didn't change the detectable depth. However to acquire our deep tissue liver maps we only used an integration time of 3 seconds per step for adequate analysis as seen in FIG. 1-4.

Quantitative Spectral Analysis.

DCLS finds the linear combination of spectra from the pure components contained in the sample that most closely matches the Raman spectrum of the sample. Pure component spectra of various SERS nanoparticles and nanotubes were acquired from a pure 5 μl sample aliquoted onto a piece of Parafilm® under the microscope. The multiplicative constants derived by the DCLS analysis are proportional to the concentration of the pure components. The DCLS method was chosen since all the Raman spectra of the pure components, background autofluorescence, SERS and SWNT nanoparticles, were available, and since those components have considerable spectral overlap. This spectral overlap makes it impossible to quantify the contribution of one component independently of the others. For our quantitative analysis, the Nanoplex™ software (Oxonica Inc., Mountain View, Calif.) was used. Before every scan, pure spectra components were taken from the SERS and SWNT nanoparticles, along with the mouse autofluorescence that was used as a background component. The DCLS method gave very accurate results since pure spectral components did not change when mixed together nor when injected into a living subject, nor did they change as function of tissue depth.

Example 2

Introduction

We employ the use of an optimized non-invasive Raman microscope to evaluate tumor targeting and localization of single wall carbon nanotubes (SWNT) in living nude mice. In this Example, Raman spectra and mapping were acquired in two groups of tumor bearing mice. The first group (experimental), inoculated with 20 million U87MG cells, received an intravenous injection of SWNTs conjugated with RGD peptide. The second group (control), inoculated with 20 million U87MG cells, received an intravenous injection of plain non-targeted SWNTs. Immediately after injection, Raman imaging commenced at various time points for 30 minutes to evaluate the arrival of SWNTs in the tumor. Raman spectra were also acquired at 2, 8, 24, 48, and 72 hours of the liver, tumor and contralateral shoulder to evaluate SWNT targeting in the tumor. Pharmacokinetics of SWNTs in tumor showed constant accumulation of RGD nanotubes out to 30 minutes as opposed to plain nanotubes which showed initial arrival followed by a rapid decrease in Raman signal. Raman spectra acquired from mice receiving RGD nanotubes revealed a significant increase ($p<0.05$) in SWNT accumulation in the tumor compared to the contralateral shoulder which correlated with Raman mapping. However, control mice showed no difference in nanotube accumulation between tumor site and contralateral shoulder at all time points. This data correlated well with in-vivo and ex-vivo Raman mapping of control mice which showed little to no accumulation in tumors. These results demonstrate the potential for the development of a new non-invasive preclinical Raman modality to assess the efficacy of novel therapeutic approaches in small-animal models.

Results

Pharmacokinetics of SWNT accumulation in the tumor was evaluated with dynamic Raman imaging at various time points over 30 minutes immediately following an intravenous injection of 60 pmol of SWNTs in the experimental (RGD conjugated SWNTs) and control groups (non-conjugated SWNTs). Before intravenous injection, SWNTs were also tested for stability in mouse serum and showed good stability over a 5 day period (data not shown). Raman spectral analysis revealed consistent accumulation of SWNTs in the tumors of the experimental mice as opposed to the tumors of the control mice which showed initial accumulation of SWNTs with a rapid decrease after 20 minutes post injection (FIG. 2-1). The data points revealed a statistical difference in accumulation of SWNTs between the tumors of the experimental and control groups after 20 minutes with a $p<0.05$.

Following dynamic Raman imaging, Raman mapped images of the tumor area were acquired in both groups with a raster scan at 2, 8, 24, 48, and 72 hours post-injection with a step size of 750 microns and an integration time of 3 seconds. The images acquired from the experimental mice receiving conjugated RGD nanotubes showed increased Raman signal at all time points in the tumor area suggesting effective targeting of the RGD nanotubes to the integrin expressing tumor (U87MG cell line). Notice how the tumor is easily defined and the intensity remained constant throughout all time points out to 72 hours in the experimental group (FIG. 2-2). Conversely, the Raman images acquired from the tumor area of the control group showed either minimal or no Raman signal from the non-targeted nanotubes with no identifiable tumor margins.

Figures 1, 2, 3:
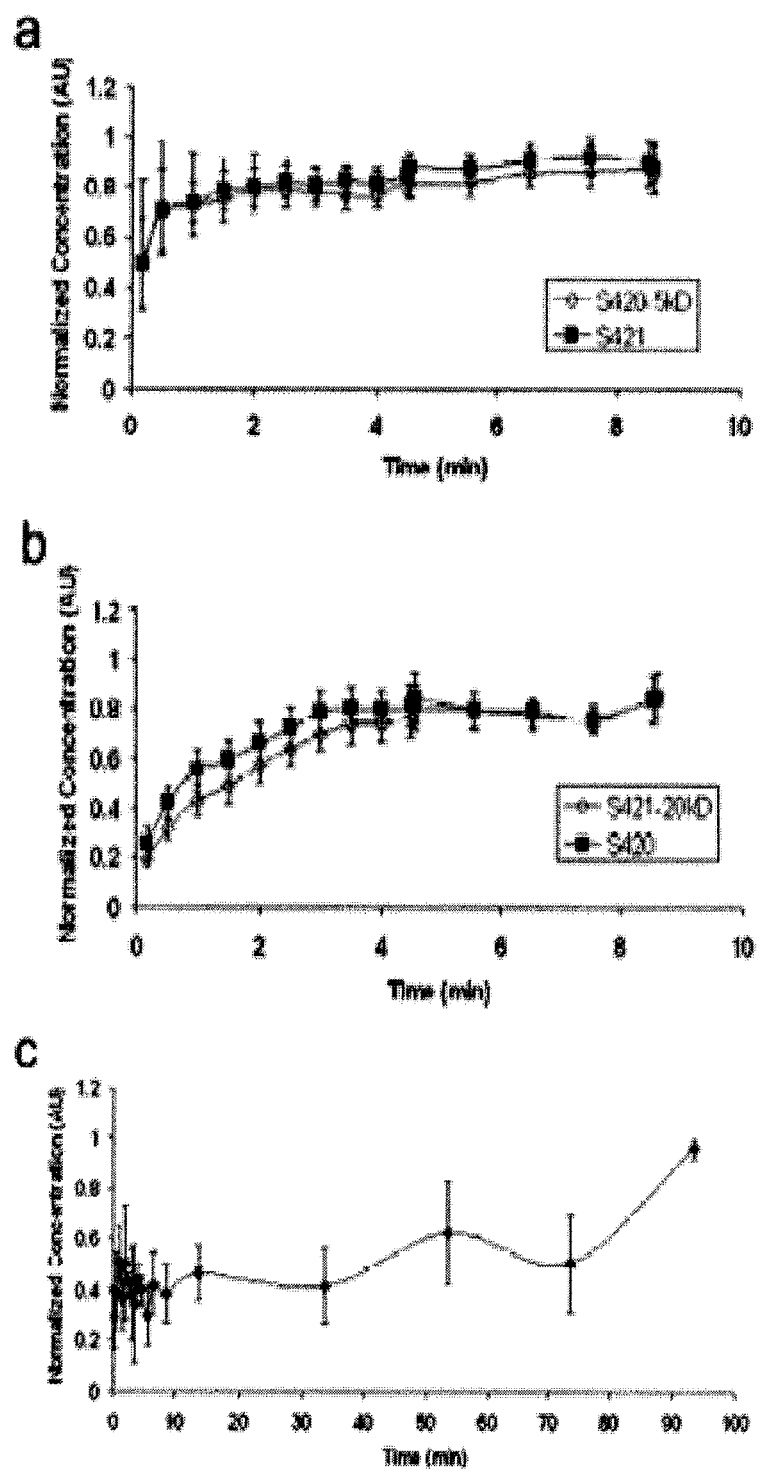

Raman spectra of tumors were also acquired and processed at 2, 8, 24, 48, and 72 hours post-injection of SWNTs for quantitative analysis. Mice in the experimental group which received RGD conjugated SWNTs showed a trend where nanotubes increased in accumulation in the tumor over 24 hours and then continued to stay in the tumor out to 72 hours post-injection. The control group that received non-targeted nanotubes showed little to no accumulation of SWNTs in the tumor from 2 to 72 hours post-injection. Statistical analysis showed a significant difference ($p<0.05$) between the accumulation of SWNTs in the tumors of experimental and control groups at all time points (FIG. 2-3). This correlated with the kinetics data where decreased accumulation of nanotubes in the control group was observed in the tumor after 20 minutes post-injection.

Figures 1, 2, 3, 4:
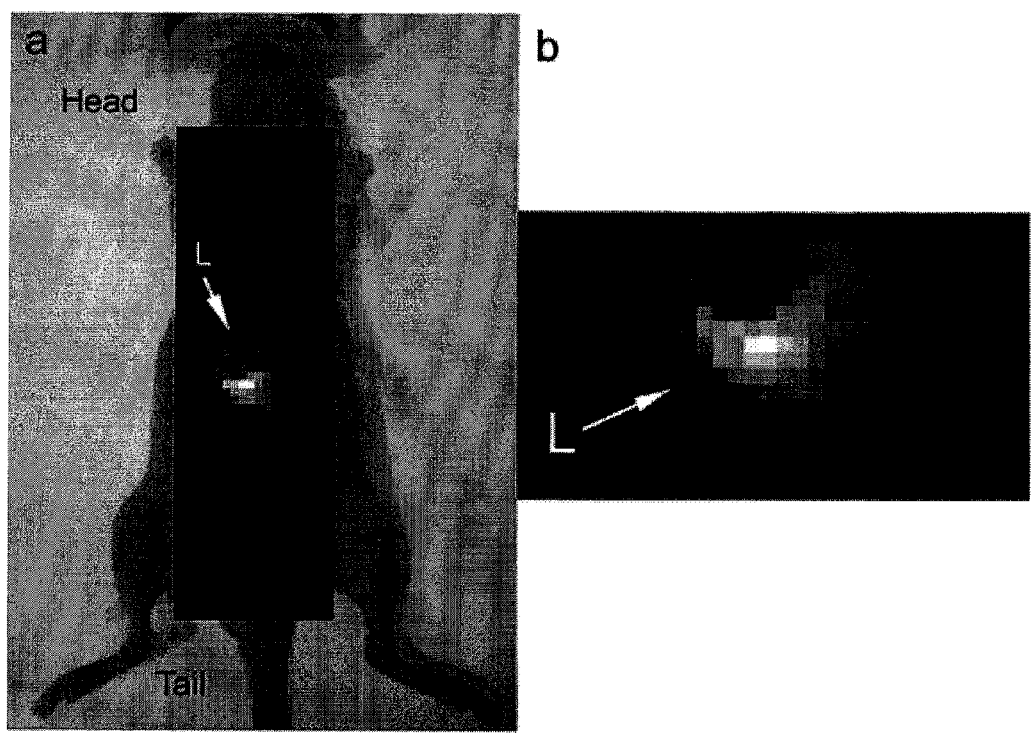
Figures 1, 2, 3, 4, 5:
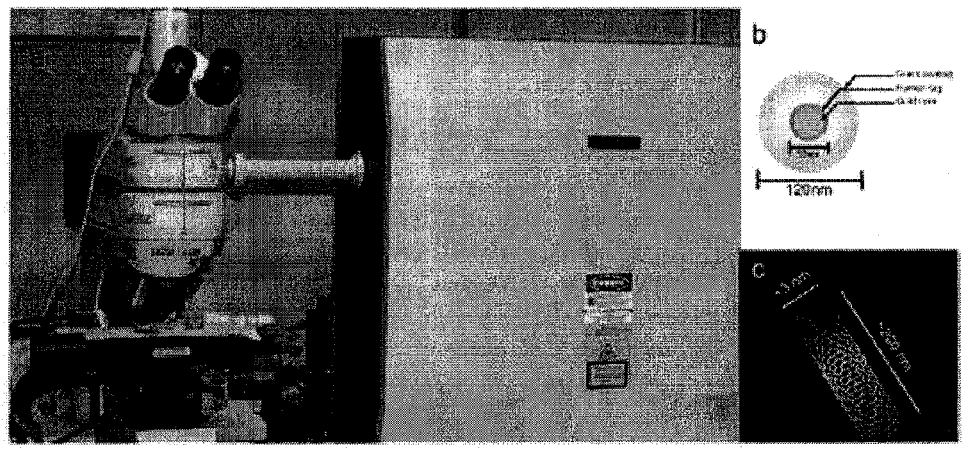
Figures 1, 2, 3, 4, 5, 6:
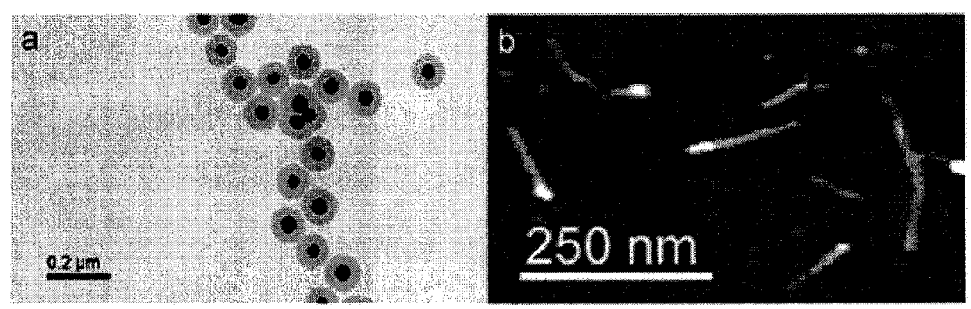
Figures 1, 2, 3, 4, 5, 6, 7:
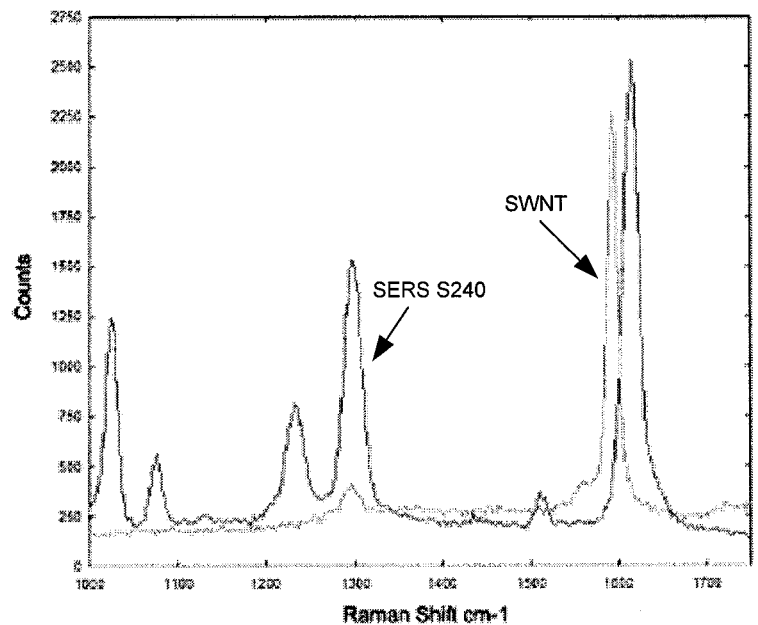
Figures 1, 2, 3, 4, 5, 6, 7, 8:
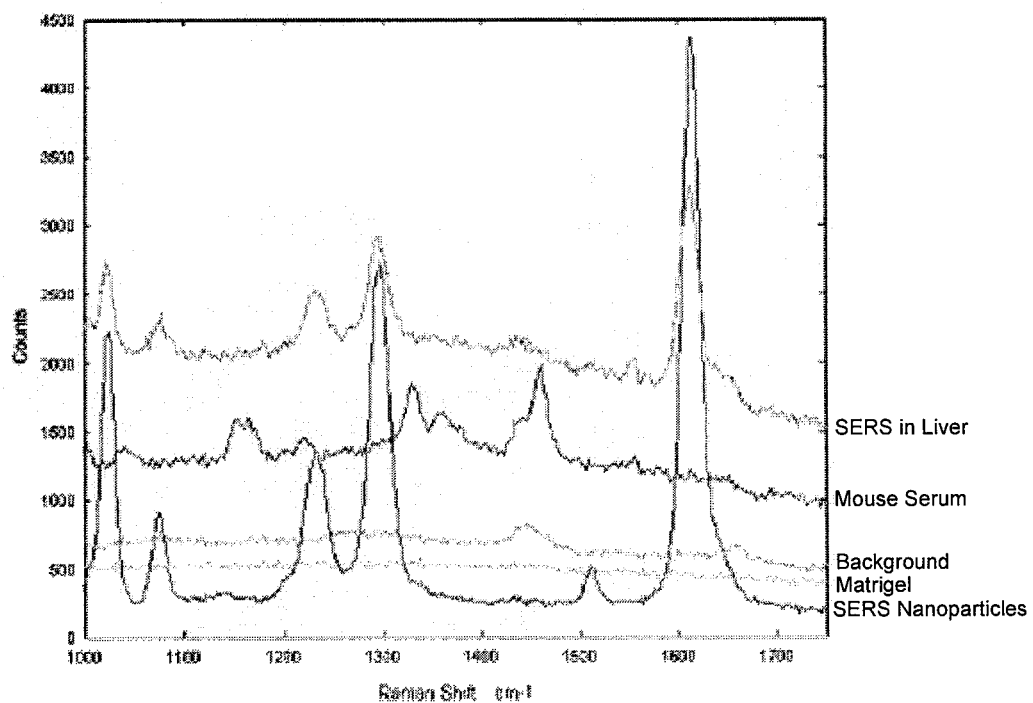
Figures 1, 2, 3, 4, 5, 6, 7, 8, 9:
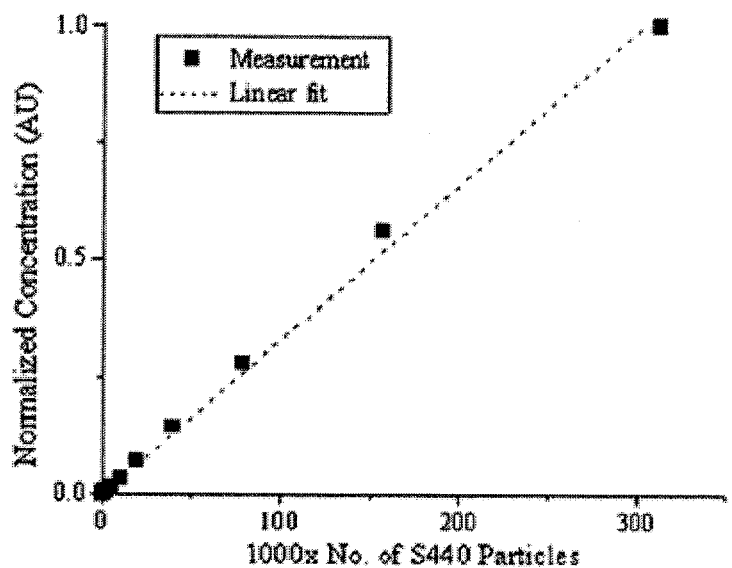
Figures 1, 2, 3, 4, 5, 6, 7, 8, 9, 10:
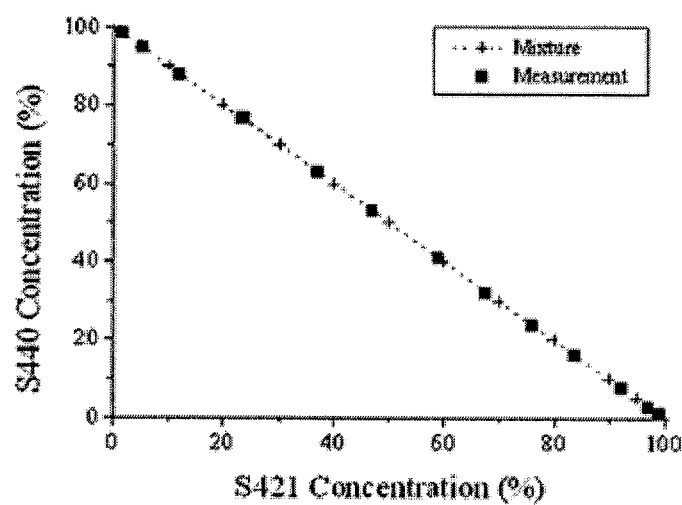
Figures 1, 2, 3, 4, 5, 6, 7, 8, 9, 10, 11:
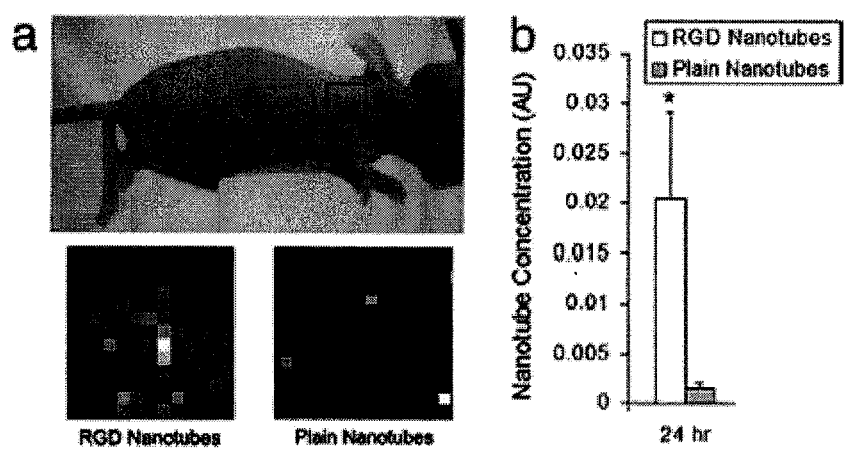
Figures 1, 2, 3, 4, 5, 6, 7, 8, 9, 10, 11, 12:
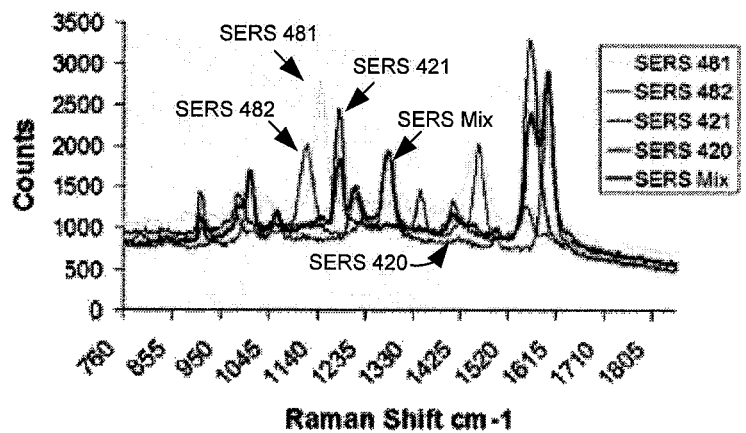
Figures 1, 2, 3, 4, 5, 6, 7, 8, 9, 10, 11, 12, 13:
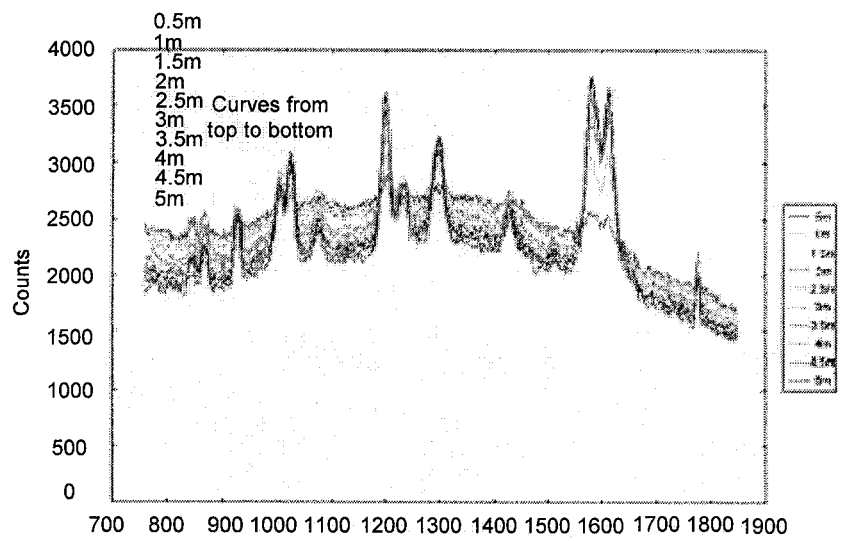
Figures 1, 2:
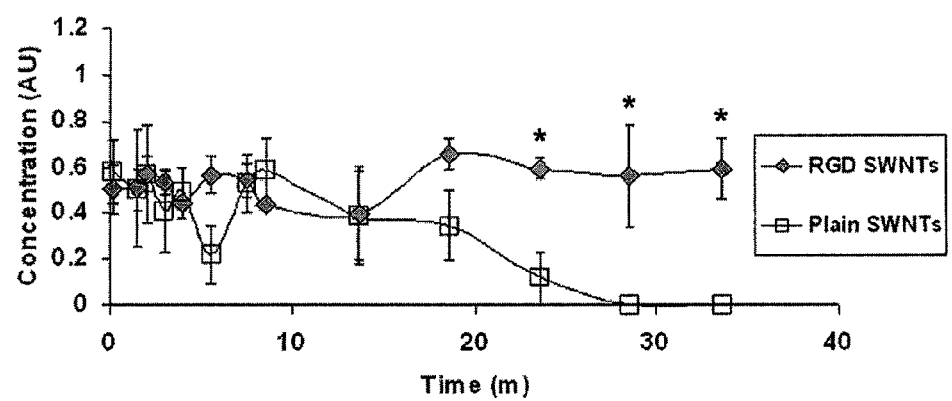
Figure 2:
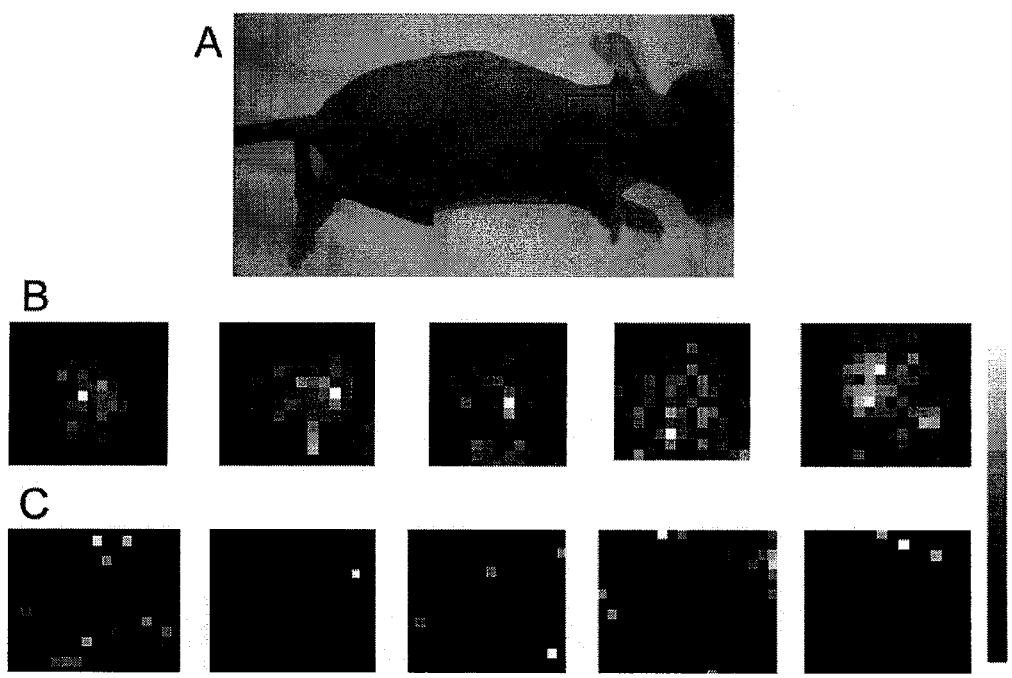
Figures 2, 3:
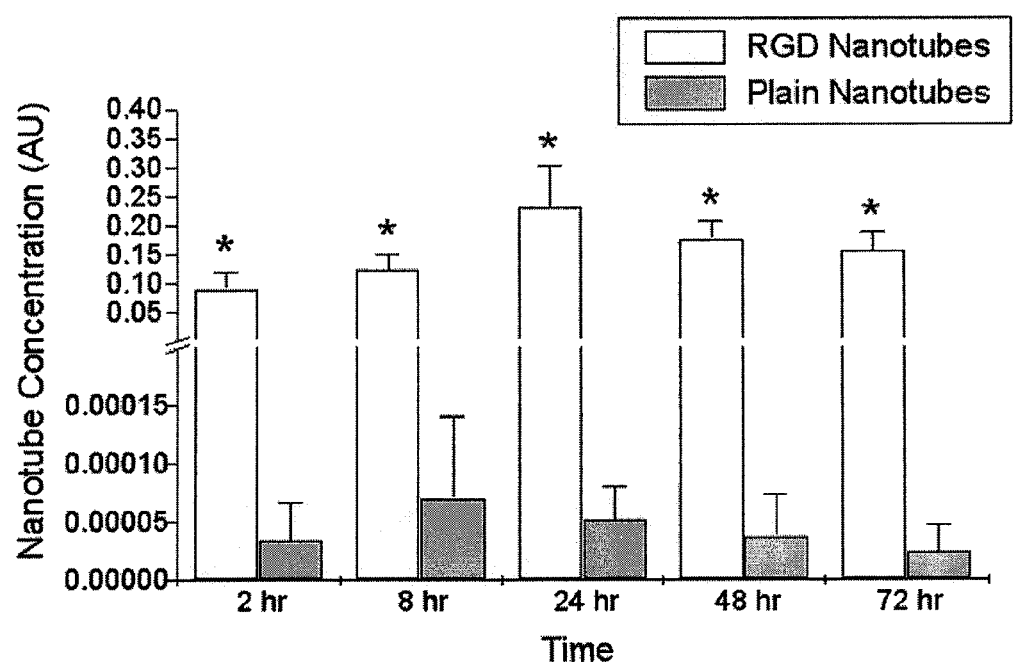
Figures 2, 3, 4:
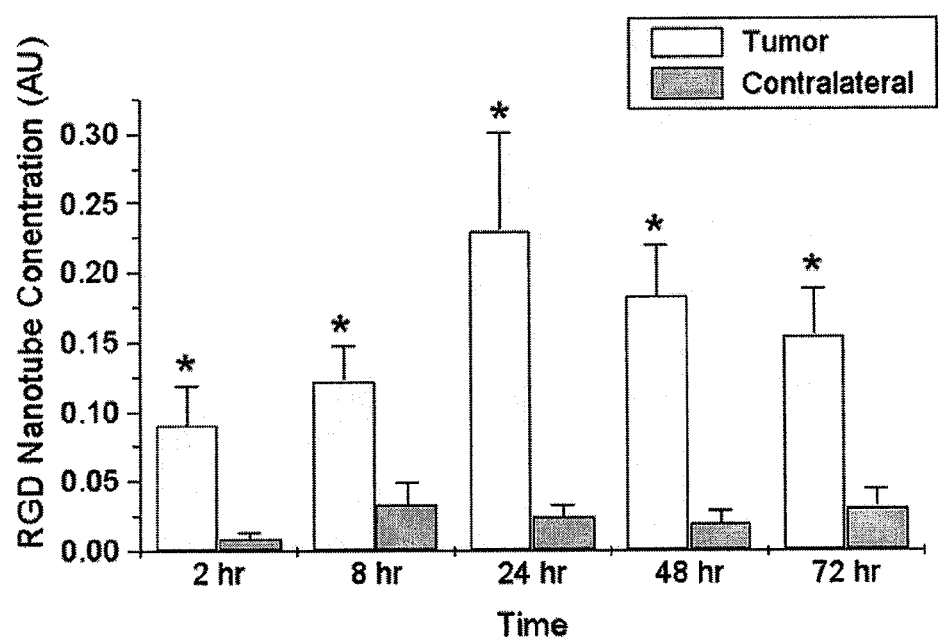
Figures 2, 3, 4, 5:
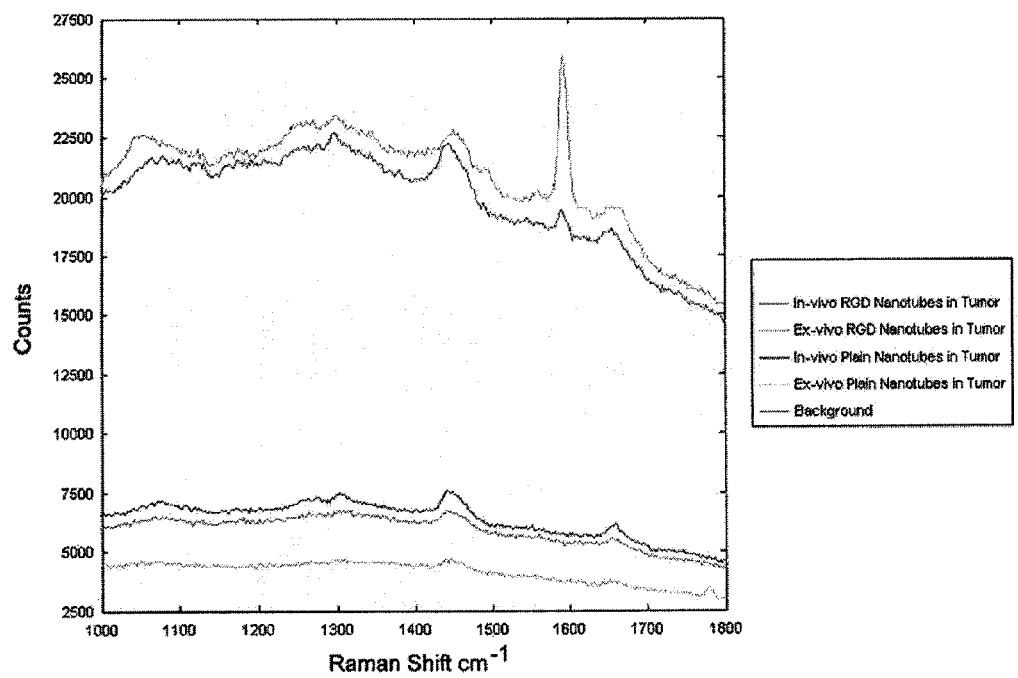
Figures 2, 3, 4, 5, 6, 6B:
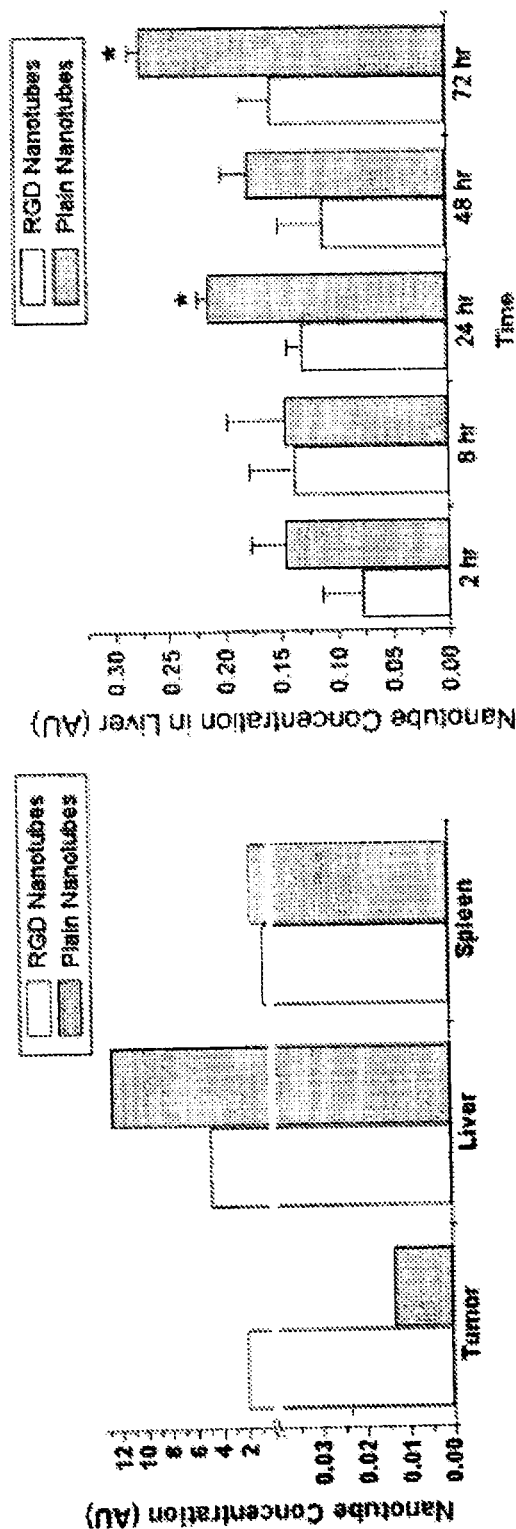
Figures 2, 3, 4, 5, 6, 7:
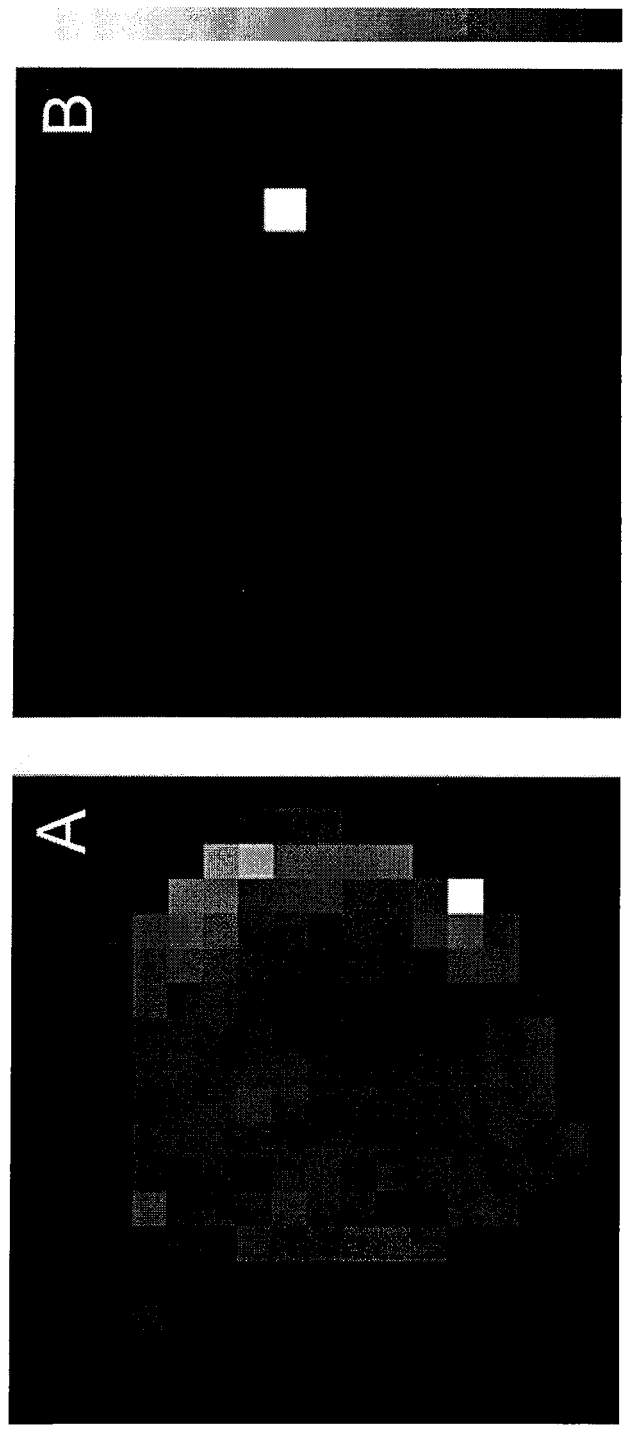
Figures 2, 3, 4, 5, 6, 7, 8:
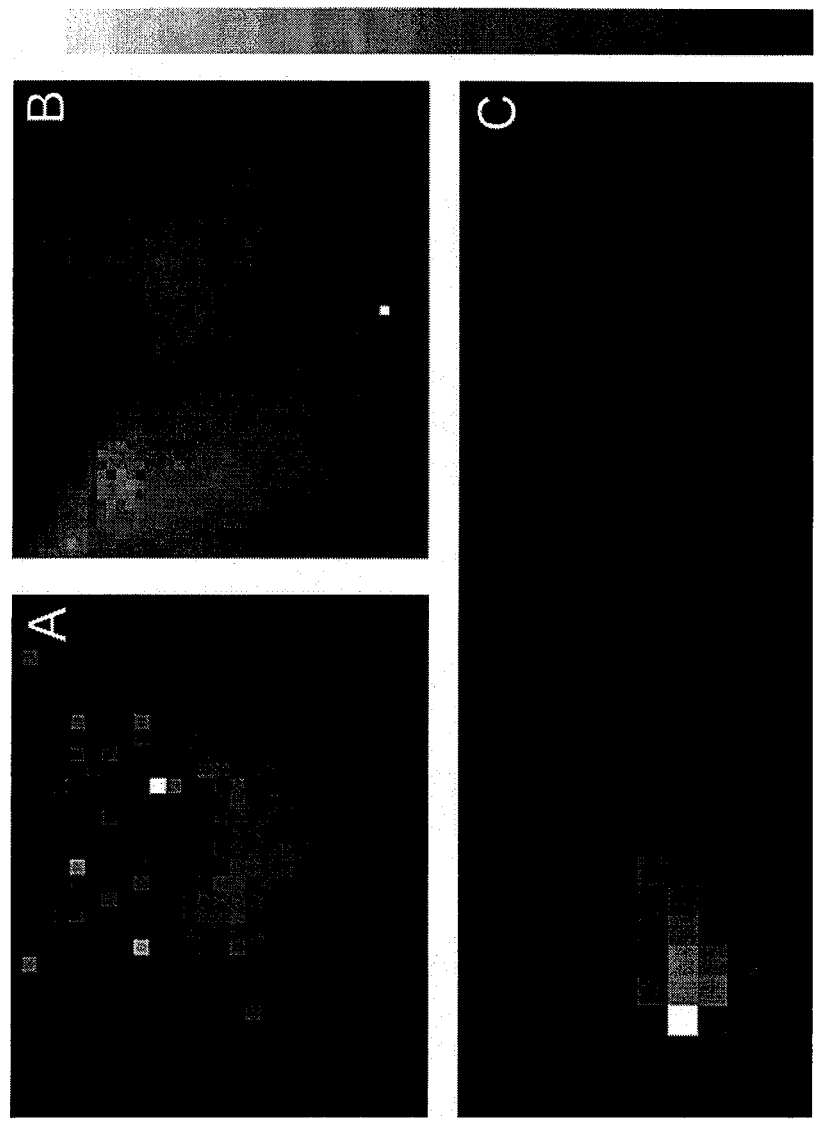

Raman spectra of the contralateral shoulder in each group were also acquired at 2, 8, 24, 48, and 72 hours post-injection to determine any non-specific localization of SWNTs in the shoulder area. This data revealed little to no accumulation of the RGD conjugated nanotubes or the non-targeted nanotubes in the contralateral shoulder. Comparisons between the tumor and contralateral shoulder in the experimental group showed a significant difference at all the time points (FIG. 2-4). However no difference was seen between the tumor and contralateral shoulder in the control group as was expected (data not shown). These results suggest that non-specific targeting of the SWNTs is minimal and shouldn't influence the increased accumulation of RGD conjugated nanotubes seen in the tumor.

Overall, these quantitative results obtained from the Raman spectra of both experimental and control groups correlated well with the Raman maps of the tumor area shown in FIG. 2-2 and support the non-invasive imaging potential of our modified Raman microscope to be developed as a preclinical imaging modality.

After the 72 hour time point, mice were sacrificed and the liver, spleen and tumor were collected for Raman imaging and histopathological examination. The ex-vivo Raman spectra of the tumor correlated well with the in-vivo Raman data collected at 72 hours as seen in FIG. 2-5. Raman mapping of the excised tumor (FIG. 2-7(A)) also revealed well defined localization of the RGD conjugated SWNTs in the tumor as opposed to the mice receiving non-targeted nanotubes which showed little to no localization in the tumor (FIG. 2-7(B)). Raman spectra analysis and mapping revealed nanotube accumulation in the excised liver and spleen of both experimental and control animals (FIG. 2-8). This is attributed to the short circulation time of these nanoparticles and natural uptake of SWNTs by the reticuloendothelial system. However a trend was observed where the ex-vivo Raman data shown in FIG. 2-6A suggested that the control group had more nanotube accumulation in the liver than the experimental group. This also correlated with the in-vivo Raman data taken from the liver in both groups as shown in FIG. 2-6B. Mice receiving non-targeted nanotubes showed more accumulation of nanotubes in the liver than the mice receiving RGD nanotubes at 24 and 72 hours with a $p<0.05$. These results support the idea that because more RGD conjugated nanotubes accumulated in the tumor; less would be found in the liver when compared to the non-targeted nanotubes which localized almost completely in the liver and spleen of the control mice.

Discussion

In this Example we have demonstrated that Raman spectroscopy has the potential to non-invasively localize targeting of SWNTs conjugated with RGD in an integrin expressing tumor model. The Raman G-band peak (~1593 $cm^{-1}$) associated with the graphite in SWNTs was easily identified over time from the non-invasive Raman spectra acquired in the tumors of the experimental mice receiving RGD nanotubes.

Raman imaging of the excised tumor and histopathological examination supported this non-invasive Raman data revealing the presence of RGD nanotube clusters in the tumor at 72 hours post-injection. The lack of nanotube accumulation in the tumors of the control mice receiving non-targeted nanotubes was determined by the less intense to complete absence of the 1593 cm$^{-1}$ Raman peak both in-vivo and ex-vivo. Pathological examination of these control mice revealed no trace of nanotubes in the tumor; however several nanotube clusters were found in the liver.

Thus far, the role of Raman spectroscopy in biomedical applications has been mostly limited to ex-vivo evaluation of cells and excised tissues ((2000) *Phys Med Biol* 45, R1-59; (2005) *Proc Natl Acad Sci USA* 102, 12371-6; (2006) *Anal Chem* 78, 7211-5; (2007) *Anal Chem* 79, 916-22; and (2006) *Nano Lett* 6, 2225-31, each of which is incorporated herein by reference for the corresponding discussion). Non-invasive Raman spectroscopy could provide longitudinal information in living subjects at various time points without having to sacrifice several animals. This relatively cheap and easy to use imaging system could also be used in conjunction with other imaging modalities such as microPET or MRI to achieve the ultimate sensitivity and specificity. Multimodal biomedical imaging can provide another degree of evidence to support the efficacy of novel therapeutic techniques. Investigators have recently developed SWNT/iron oxide nanoparticle complexes as multimodal biomedical imaging agents, combining the high contrast imaging power of MRI and the sensitivity of Raman ((2007) *Nano Lett* 7, 861-867, each of which is incorporated herein by reference for the corresponding discussion). A therapeutic potential also exists through phototherapy and hyperthermia effects with NIR laser excitation, and high frequency external magnetic field modulation.

Although other Raman nanoparticles exist, as mentioned above, carbon nanotubes have the added advantage of having an inherent Raman signature. No further labeling or encapsulation is needed to produce a Raman peak. Raman spectroscopy has proven to be a valuable tool for characterizing SWNTs. For instance, Raman spectroscopy has been used to differentiate between metallic and semi-conducting nanotubes, and may also be employed to determine SWNT diameters and even nanotube chirality ((2004) *J Nanosci Nanotechnol* 4, 691-703 and (2003) *J Nanosci Nanotechnol* 3, 19-37, each of which is incorporated herein by reference for the corresponding discussion). One paper discusses the use of Raman spectroscopy to differentiate between double wall nanotubes (DWNTs) and triple wall nanotubes (TWNTs) ((2007) *Chem Commun (Camb)*, 1092-4), which is incorporated herein by reference for the corresponding discussion. Several new Raman peaks are seen in the radial breathing mode (RBM) region of the Raman spectrum for TWNTs.

One problem that exists when using nanotubes in conjunction with Raman spectroscopy is their lower sensitivity when compared with COINS and SERS nanoparticles. It was determined by our lab that nanotubes are roughly 1400 times less sensitive than SERS nanoparticles. However, it has been recently reported that carbon nanotubes adsorbed onto metal surfaces increase their Raman signal (Hu, X., Wang, T., Wang, L., Guo, S. & Dong, S. (2007) Langmuir, which is incorporated herein by reference for the corresponding discussion). The introduction of silver nanoparticles into the carbon nanotubes film results in the SERS effect increasing the intensity of the Raman spectrum. This plasmonic phenomenon is referred to as surface enhanced Raman scattering (SERS) where molecules adsorbed onto nano-roughened noble metal surfaces experience a dramatic increase in the incident electromagnetic field producing high Raman intensity. SERS enhances detection sensitivity up to 10-14 orders of magnitude over conventional Raman spectroscopy and is employed in both COINs and SERS nanoparticles ((2003) *Langmuir* 19, 4784-4790; (2005) Nano Lett 5, 49-54; and (2007) *Nano Lett* 7, 351-6, each of which are incorporated herein by reference for the corresponding discussion).

Methods

Animal Experiments

Female nude mice (Charles River) were used for all Raman spectroscope studies. All procedures performed on the animals were approved by the Stanford University Institutional Animal Care and Use Committee, and within the guidelines of humane care of laboratory animals.

Animal Model

U87MG human glioblastoma (American Type Culture Collection, ATCC) were cultured under standard conditions. The U87MG tumor models were generated by subcutaneous injection of $20\times10^6$ cells in 200 μl PBS into the front right arm of the mice. In-vivo Raman spectroscopic measurements were taken of living mice when the tumor volume reached approximately 200 mm$^3$.

Preparation and Conjugation of Pegylated SWNTs with RGD

Single wall nanotubes were prepared as described by Liu et al Nature 2006, which is incorporated by reference for the corresponding discussion. The SWNT had dimensions of a few nanometers in diameter and approximately 200 nm in length yielding a concentration of 300 nM and a molecular weight of 170 kDa.

Animal Injections

Three tumor bearing mice were subcutaneously injected with 60 pmol (10 μg) of SWNTs ($3.6\times10^{13}$ nanotubes) conjugated with RGD and PEG in a 200 μl volume using a 26 gauge needle. Three separate tumor bearing mice were injected via tail-vein with 60 pmol (10 μg) of plain SWNTs ($3.6\times10^{13}$ nanotubes) with PEG in a 200 μl volume using a 26 gauge needle.

Raman Spectroscopic Imaging in Living Mice

Raman measurements were performed with a modified Renishaw microscope system (Keren, S., Zavaleta, C. L., Cheng, Z., Gheysens, O. & Gambhir, S. S. (2007) *Nat Med*, submitted April 2007, which is incorporated herein by reference for the corresponding discussion). A semiconductor diode near-infrared laser operating at λ=785 nm was used as the excitation source with a laser power of 100 mW. Raman images were obtained by using a Raman point mapping method. A computer-controlled x-y translation stage was used to raster-scan the mouse, creating a spectral image by measuring the Raman spectrum of each individual pixel in the area of interest with a 750 μm step size. The objective lens used was a 12× open field in a dimly lit room.

Tissue Collection

At 72 hours post-injection randomly selected mice were sacrificed from each group and tissues of interest (tumor, liver, spleen) were excised for Raman imaging. Tissues were immediately fixed in 10% formalin and raster scanned with a\our optimized Raman microscope to acquire a Raman image.

Quantitative Spectral Analysis

The direct classical least squares (DCLS) method, also called linear unmixing and K-matrix methods, was used in this work to perform a quantitative analysis of Raman spectroscopy ((1980) *Appl Spec* 34, 539-548 and (2003) *Appl Spect* 57, 20A-42A, each of which are incorporated herein by reference for the corresponding discussion). DCLS finds the linear combination of spectra from the pure components contained in the sample that most closely matches the Raman spectrum of the sample. Pure component spectra of various SERS nanoparticles and nanotubes were acquired from a pure 5 μl sample aliquoted onto a piece of Parafilm® under the microscope. The multiplicative constants derived by the DCLS analysis are proportional to the concentration of the pure components. The DCLS method was chosen since all the Raman spectra of the pure components, background autofluorescence, SERS and SWNT nanoparticles, were available, and since those components have considerable spectral overlap. This spectral overlap makes it impossible to quantify the contribution of one component independently of the others. For our quantitative analysis, the Nanoplex™ software (Oxonica Inc., Mountain View, Calif.) was used. Before every scan, pure spectra components were taken from the SERS and SWNT nanoparticles, along with the mouse autofluorescence that was used as a background component. The DCLS method gave very accurate results since pure spectral components did not change when mixed together nor when injected into a living subject, nor did they change as function of tissue depth.

Statistical Analysis

The data collected from these experiments were analyzed for statistical differences using a 95% confidence interval (p<0.05) using Graph Pad Prism 5 Software. A student's t-test was used to compare the data of the experimental group to the data of the control group. An equality of variances test was performed and revealed little variance between the groups. Therefore, a one-tailed t-test assuming equal variances was performed to determine statistical significance because it was hypothesized that the experimental group would have higher Raman signal (concentration) in the tumor area than the control group due to targeting potential. The values reported appear as mean ±standard error or mean (SEM). A Bonferroni correction was not performed because it was too conservative since the data from each of the time points correlated well with each other, and there was little chance of getting a significant result from multiple t-testing.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

We claim:

1. A method of imaging a tissue in a living host, comprising:
   administering the living host with a Raman nanoparticle; and
   imaging the tissue in the living host with a Raman imaging system using raster scanning, wherein the Raman nanoparticle is a single-wall carbon nanotube.

2. The method of claim 1, wherein the single-wall carbon nanotube has a diameter of about 1 to 5 nm and a length of about 50 to 500 nm.

3. The method of claim 1, wherein imaging includes:
   imaging the tissue with the Raman imaging system to produce a Raman image; and the method further comprising:
   imaging the tissue with an anatomical imaging system to produce an anatomical image; and
   combining the Raman image with the anatomical image to form a multimodality image.

4. The method of claim 3, wherein the anatomical imaging system is selected from: computer topography (CT) imaging system, ultra sound imaging system, magnetic resonance imaging (MRI) system, or combinations thereof.

5. The method of claim 3, further comprising:
   administering the living host with a Raman nanoparticle.

6. The method of claim 1, wherein the tissue is a deep tissue.

7. The method of claim 6, wherein the deep tissue is an organ.

8. A method of deep tissue imaging in a living host, comprising:
   administering the living host with a Raman nanoparticle;
   imaging the deep tissue in the living host with a Raman imaging system to produce a Raman image;
   imaging the deep tissue with an anatomical imaging system to produce an anatomical image; and
   combining the Raman image with the anatomical image to form a multimodality image.

9. The method of claim 8, wherein imaging includes:
   imaging the tissue with the Raman imaging system by raster scanning a portion of or an entirety of the tissue; and
   generating an image of the tissue.

10. The method of claim 9, further comprising:
    administering the living host with a Raman nanoparticle.

11. The method of claim 8, wherein the Raman nanoparticle is selected from surface enhanced Raman scattering (SERS) nanoparticles, nanotubes, composite organic inorganic nanoparticles (COINS), or combinations thereof.

12. The method of claim 8, wherein the Raman nanoparticle is a surface enhanced spectroscopy-active composite nanoparticle.

13. The method of claim 12, wherein the surface enhanced spectroscopy-active composite nanoparticle has a core, a Raman-active compound, and a coating.

14. The method of claim 13, wherein the core is selected from: gold, silver, or copper.

15. The method of claim 13, wherein the Raman-active compound is selected from: 4-mercaptopyridine (4-MP); trans-4,4'bis(pyridyl)ethylene (BPE); quinolinethiol; 4,4'-dipyridyl, 1,4-phenyldiisocyanide; mercaptobenzamidazole; 4-cyanopyridine; 1',3,3,3',3'-hexamethylindotricarbocyanine iodide; 3,3'-diethyltiatricarbocyanine; malachite green isothiocyanate; bis-(pyridyl)acetylenes; Bodipy; TRIT (tetramethyl rhodamine isothiol); NBD (7-nitrobenz-2-oxa-1,3-diazole); Texas Red dye; phthalic acid; terephthalic acid; isophthalic acid; cresyl fast violet; cresyl blue violet; brilliant cresyl blue; para-aminobenzoic acid; erythrosine; biotin; digoxigenin; 5-carboxy-4',5'-dichloro-2',7'-dimethoxy fluorescein; 5-carboxy-2',4',5',7'-tetrachlorofluorescein; 5-carboxyfluorescein; 5-carboxy rhodamine; 6-carboxyrhodamine; 6-carboxyletramethyl amino phthalocyanines;

azomethines; cyanines; xanthines; succinylfluoresceins; aminoacridine; fullerenes; organocyanides; or combinations thereof.

16. The method of claim 13, wherein the coating is a silica coating.

17. The method of claim 13, wherein the surface enhanced spectroscopy-active composite nanoparticle has a gold core, a Raman-active compound, and a silica coating.

18. The method of claim 8, wherein the Raman nanoparticle is a single-wall carbon nanotube.

19. The method of claim 18, wherein the single-wall carbon nanotube has a diameter of about 1 to 5 nm and a length of about 50 to 500 nm.

20. The method of claim 8, wherein the deep tissue is an organ.

* * * * *

UNITED STATES PATENT AND TRADEMARK OFFICE
CERTIFICATE OF CORRECTION

PATENT NO. : 8,795,628 B2  
APPLICATION NO. : 12/598780  
DATED : August 5, 2014  
INVENTOR(S) : Gambhir et al.

Page 1 of 1

It is certified that error appears in the above-identified patent and that said Letters Patent is hereby corrected as shown below:

At column 1, lines 22-24, in the paragraph entitled "Statement Regarding Federally Sponsored Research or Development", delete:

"This invention(s) was made with government support under Grant No. U54CA119367 awarded by the NCICCNE. the government has certain right in the invention(s)."

and replace with:

"This invention was made with Government support under contract CA119367 awarded by the National Institutes of Health. The Government has certain rights in the invention."

Signed and Sealed this  
Ninth Day of August, 2016

Michelle K. Lee  
*Director of the United States Patent and Trademark Office*